United States Patent
Hess et al.

(10) Patent No.: US 9,663,545 B2
(45) Date of Patent: May 30, 2017

(54) ORGANOMETALLIC 2-CYANO-2-AMINOBENZOATE-PROPYL DERIVATES AND THEIR USE AS ANTHELMINTICS

(71) Applicants: UNIVERSITÄT ZÜRICH, Zürich (CH); THE UNIVERSITY OF MELBOURNE, Melbourne, Victoria (AU)

(72) Inventors: Jeannine Hess, Oberkirch (CH); Malay Patra, Zürich (CH); Gilles Gasser, Zug (CH); Abdul Jabbar, Tarneit (AU); Robin B. Gasser, Werribee (AU)

(73) Assignees: UNIVERSITAT ZURICH, Zurich (CH); THE UNIVERSITY OF MELBOURNE, Melbourne (AU)

( * ) Notice: Subject to any disclaimer, the term of this patent is extended or adjusted under 35 U.S.C. 154(b) by 0 days.

(21) Appl. No.: 14/902,004

(22) PCT Filed: Jul. 1, 2014

(86) PCT No.: PCT/EP2014/064005
§ 371 (c)(1),
(2) Date: Dec. 30, 2015

(87) PCT Pub. No.: WO2015/000928
PCT Pub. Date: Jan. 8, 2015

(65) Prior Publication Data
US 2016/0368939 A1 Dec. 22, 2016

(30) Foreign Application Priority Data
Jul. 1, 2013 (EP) .................................. 13174551

(51) Int. Cl.
C07F 15/00 (2006.01)
C07F 15/02 (2006.01)
(Continued)

(52) U.S. Cl.
CPC .............. *C07F 15/02* (2013.01); *A01N 55/02* (2013.01); *C07F 13/00* (2013.01);
(Continued)

(58) Field of Classification Search
CPC .......... C07F 17/02; C07F 15/02; C07F 15/06; C07F 15/0046; C07F 13/00; A01N 55/02
(Continued)

(56) References Cited

FOREIGN PATENT DOCUMENTS

WO 2005/044784 5/2005

*Primary Examiner* — Porfirio Nazario Gonzalez
(74) *Attorney, Agent, or Firm* — Soroker Agmon Nordman

(57) ABSTRACT

The invention relates to compounds characterized by a general formula (1),

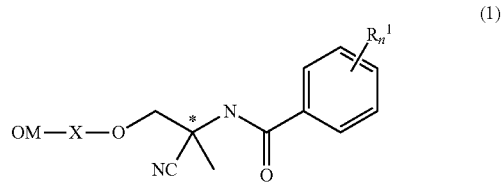

wherein X is a group described by a general formula $—K_p—F_l—K_q—$, wherein
$F_l$ is $—C(=O)—$, $—C(=S)—$, with l being 0 or 1,
$K_p$ is a $C_p$-alkyl with p being 0, 1, 2, 3 or 4,
$K_q$ is a $C_q$-alkyl with q being 0, 1, 2, 3 or 4, and wherein n of $R^1_n$ is 0, 1, 2, 3, 4 or 5, and
each $R^1$ independently from any other $R^1$ is $—C(=O)OR^2$, $—C(=O)NR^2_2$, $—C(=O)SR^2$, $—C(=S)OR^2$, $—C(NH)NR^2_2$, $CN_4H_2$, $—NR^2_2$, $—C(=O)R^2$, $—C(=S)R^2$, $—OR^2$, $—SR^2$, $—CF_3$, $—OCF_3$, $—SCF_3$, $—SOCF_3$, $—SO_2CF_3$, $—CN$, $—NO_2$, $—F$, $—Cl$, $—Br$ or $—I$, (Continued)

Figure 1:
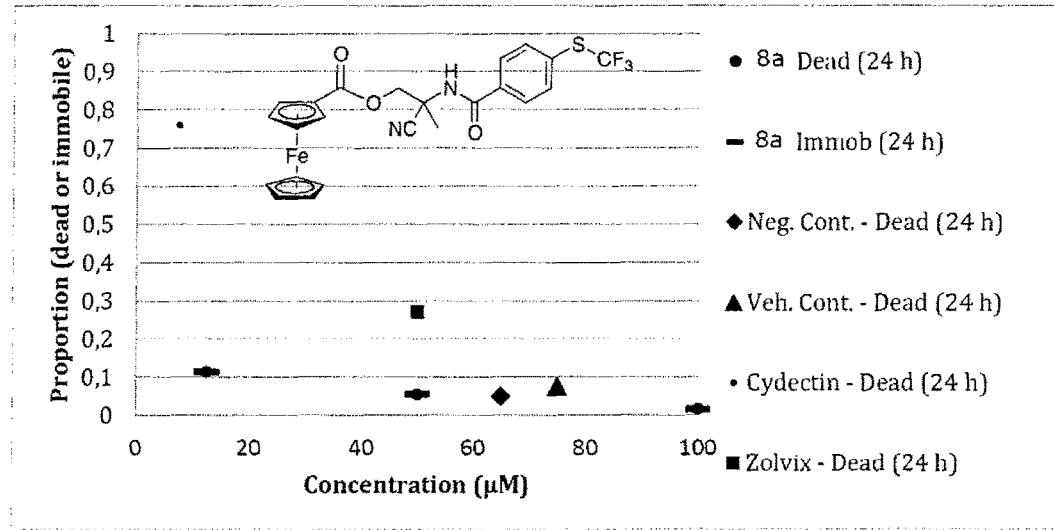

with each $R^2$ independently from any other $R^2$ being a hydrogen or $C_1$-$C_4$ alkyl, and wherein OM is an organometallic compound independently selected from the group of an unsubstituted or substituted metal sandwich compound, an unsubstituted or substituted half metal sandwich compound or a metal carbonyl compound and their use in a method for treatment of infections by helminths.

15 Claims, 2 Drawing Sheets

(51) Int. Cl.
  *C07F 17/02* (2006.01)
  *C07F 15/06* (2006.01)
  *C07F 13/00* (2006.01)
  *A01N 55/02* (2006.01)

(52) U.S. Cl.
  CPC .......... *C07F 15/0046* (2013.01); *C07F 15/06* (2013.01); *C07F 17/02* (2013.01)

(58) Field of Classification Search
  USPC ...................................... 556/48, 59, 60, 145
  See application file for complete search history.

ORGANOMETALLIC 2-CYANO-2-AMINOBENZOATE-PROPYL DERIVATES AND THEIR USE AS ANTHELMINTICS

RELATED APPLICATIONS

The present application claims priority as a US national phase under 35 U.S.C. 363 of PCT/EP2014/064005 filed on Jul. 1, 2014, the disclosure of which is incorporated herein by reference.

FIELD OF THE INVENTION

The present invention relates to organometallic 2-cyano-2-aminobenzoate-propyl derivatives and their use as anthelmintics.

BACKGROUND OF THE INVENTION

Parasites cause significant economic losses to agriculture worldwide due to poor productivity, limited growth rates and death. According to some estimates, the financial damage caused by parasites to the livestock industry is in the order of tens of billions of dollars per annum. Decreased productivity influences not only the livestock industry but also substantially affects global food production. Moreover, in spite of the anthelmintic drugs discovered and marketed in the last decades, problems of parasitic worms persist and multi-drug resistance to most classes of anthelmintics is widespread. The development of new classes of anthelmintics is a major priority. Any anthelmintic developed for parasites of livestock would also have application to parasites of humans and other animals, including companion animals, such as dogs, cats and equids. One sixth of the human population in earth is affected chronically by at least one parasitic helminth, and the socioeconomic burden (in DALYs) is greater than that of cancer and diabetes. Some helminths, such as *Schistosoma haematobium*, *Opisthorchis viverrini* and *Clonorchis sinensis* induce malignant cancers in humans.

Recently, a new class of synthetic anthelmintics referred to as Amino-Acetonitrile Derivatives (AADs, see WO2005/044784A1), has been commercially developed under the trade name Zolvix® for the treatment of infected sheep. Monepantel (AAD 1566)

AAD 1566

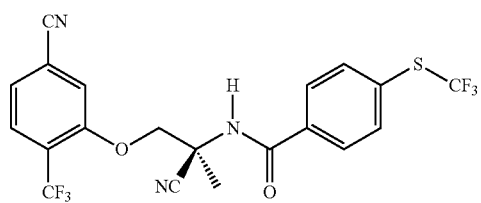

The precise mode of action of monepantel is not yet elucidated, although an interaction of AADs with a specific acetylcholine receptor (nAChR) subunit has been proposed. This target is only present in nematodes but not in mammals, making it relevant for the development of a new class of anthelmintic drugs. Of high importance, a mutant of *Haemonchus contortus* with a reduced sensitivity to monepantel was recently identified using a novel in vitro selection procedure (L. Rufener, R. Baur, R. Kaminsky, P. Maeser and E. Sigel, Mol. Pharmacol., 2010, 78, 895-902), indicating that resistance will develop in gastrointestinal nematodes of livestock. This observation has been noticed for all current anthelmintics on the market. In light of the above referenced state of the art, the objective of the present invention is to provide novel compounds to control parasites of human beings and livestock.

This objective is attained by the subject-matter of the independent claims.

SUMMARY OF THE INVENTION

According to a first aspect of the invention provided herein are organometallic compounds characterized by a general formula (1),

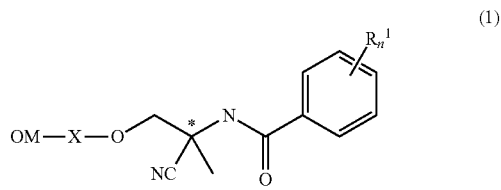

(1)

wherein X is a group described by a general formula —$K_p$—$F_l$—$K_q$—, wherein
  $F_l$ is —C(=O)—, —C(=S)—, with l being 0 or 1,
  $K_p$ is a $C_p$-alkyl with p being 0, 1, 2, 3 or 4,
  $K_q$ is a $C_q$-alkyl with q being 0, 1, 2, 3 or 4, and wherein n of $R^1_n$ is 0, 1, 2, 3, 4 or 5, and
  each $R^1$ independently from any other $R^1$ is —C(=O)O$R^2$, —C(=O)N$R^2_2$, —C(=O)S$R^2$, —C(=S)O$R^2$ —C(NH)N$R^2_2$, CN$_4$H$_2$, —N$R^2_2$, —C(=O)$R^2$, —C(=S)$R^2$, —O$R^2$, —S$R^2$, —CF$_3$, —OCF$_3$, —SCF$_3$, —SOCF$_3$, —SO$_2$CF$_3$, —CN, —NO$_2$, —F, —Cl, —Br, or —I,
  with each $R^2$ independently from any other $R^2$ being hydrogen or $C_1$-$C_4$ alkyl, and wherein
  OM is an organometallic compound selected from the group of an unsubstituted or substituted metal sandwich compound, an unsubstituted or substituted half metal sandwich compound or a metal carbonyl compound.

The term "substituted" refers to the addition of a substituent group to a parent compound.

"Substituent groups" can be protected or unprotected and can be added to one available site or to many available sites in a parent compound. Substituent groups may also be further substituted with other substituent groups and may be attached directly or by a linking group such as an alkyl or hydrocarbyl group to a parent compound. "Substituent groups" amenable herein include, without limitation, halogen, oxygen, nitrogen, sulphur, hydroxyl, alkyl, alkenyl, alkynyl, acyl (—C(O)$R^a$), carboxyl (—C(O)O$R^a$), aliphatic groups, alicyclic groups, alkoxy, substituted oxy (—O$R^a$), aryl, aralkyl, heterocyclic radical, heteroaryl, heteroarylalkyl, amino (—N($R^b$)($R^c$)), imino (=N$R^b$), amido (—C(O)N($R^b$)($R^c$) or —N($R^b$)C(O)$R^a$), hydrazine derivates (—C(NH)NR$^a$R$^b$), tetrazole (CN$_4$H$_2$), azido (—N$_3$), nitro (—NO$_2$), cyano (—CN), isocyano (—NC), cyanato (—OCN), isocyanato (—NCO), thiocyanato (—SCN); isothiocyanato (—NCS); carbamido (—OC(O)N($R^b$)($R^c$) or —N($R^b$)C(O)O$R^a$), thiol (—S$R^b$), sulfinyl (—S(O)$R^b$), sulfonyl (—S(O)$_2$$R^b$), sulfonamidyl (—S(O)$_2$N($R^b$)($R^c$) or —N(R$^b$)S(O)$_2$R$^b$) and fluorinated compounds —CF$_3$, —OCF$_3$, —SCF$_3$, —SOCF$_3$ or —SO$_2$CF$_3$. Wherein each R$^a$, R$^b$ and R$^c$ is, independently, H or a further substituent group with a preferred list including without limitation, H, alkyl, alkenyl, alkynyl, aliphatic, alkoxy, acyl, aryl, heteroaryl, alicyclic, heterocyclic and heteroarylalkyl.

As used herein the term "alkyl," refers to a saturated straight or branched hydrocarbon moiety containing up to 10, particularly up to 4 carbon atoms. Examples of alkyl groups include, without limitation, methyl, ethyl, propyl, butyl, isopropyl, n-hexyl, octyl, decyl and the like. Alkyl groups typically include from 1 to about 10 carbon atoms (C$_1$-C$_{10}$ alkyl), particularly with from 1 to about 4 carbon atoms (C$_1$-C$_4$ alkyl). The term "cycloalkyl" refers to an interconnected alkyl group forming a ring structure. Alkyl or cycloalkyl groups as used herein may optionally include further substituent groups.

As used herein the term "alkenyl," refers to a straight or branched hydrocarbon chain moiety containing up to 10 carbon atoms and having at least one carbon-carbon double bond. Examples of alkenyl groups include, without limitation, ethenyl, propenyl, butenyl, 1-methyl-2-buten-1-yl, dienes such as 1,3-butadiene and the like. Alkenyl groups typically include from 2 to about 10 carbon atoms, more typically from 2 to about 4 carbon atoms. Alkenyl groups as used herein may optionally include further substituent groups.

As used herein the term "alkynyl," refers to a straight or branched hydrocarbon moiety containing up to 10 carbon atoms and having at least one carbon-carbon triple bond. Examples of alkynyl groups include, without limitation, ethynyl, 1-propynyl, 1-butynyl, and the like. Alkynyl groups typically include from 2 to about 10 carbon atoms, more typically from 2 to about 4 carbon atoms. Alkynyl groups as used herein may optionally include further substituent groups.

As used herein the term "alkoxy," refers to an oxygen-alkyl moiety, wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. The term "cycloalkoxy" refers to an interconnected alkoxy group forming a ring structure. Alkoxy or cycloalkoxy groups as used herein may optionally include further substituent groups.

As used herein the term "aryl" refers to a hydrocarbon with alternating double and single bonds between the carbon atoms forming a ring structure (in the following an "aromatic hydrocarbon"). The term "heteroaryl" refers to aryl compounds in which at least one carbon atom is replaced with an oxygen, a nitrogen or a sulphur atom. The aromatic hydrocarbon may be neutral or charged. Examples of aryl or hetero aryl groups are benzene, pyridine, pyrrole or cyclopenta-1,3-diene-anion. Aryl or hetero aryl groups as used herein may optionally include further substituent groups.

As used herein the term "organometallic compound" refers to a compound comprising a metal, in particular a transition metal (a metal selected from the group 3 to group 12 metals of the periodic table), as well as a metal-carbon bond.

As used herein the term "metal sandwich compound" refers to a compound comprising a metal, in particular a transition metal, bound to two aryl or heteroaryl ligands (in the following "sandwich ligands") by a haptic covalent bound. The aryl or heteroaryl ligands may be unsubstituted or substituted.

As used herein the term "half metal sandwich compound" refers to a compound comprising a metal, in particular a transition metal, bound to just one aryl or heteroaryl ligand (sandwich ligand). The other ligand may comprise—without being limited to—alkyl, allyl, CN or CO, in particular CO.

As used herein the term "metal carbonyl compound" refers to a coordination complex of at least one transition metal with a carbon monoxide (CO) ligand. It may comprise a neutral, anionic or cationic complex. The carbon monoxide ligand may be bond terminally to a single metal atom or may be bridging to two or more metal atoms. The complex may be homoeleptic (containing only carbon monoxide ligands) or heteroeleptic.

As used herein the term "metallocene" refers to a metal sandwich compound comprising an aryl or heteroaryl five ring ligand (in the following "cp-ligand" or "hetero cp-ligand").

In some embodiments, the organometallic compound may be attached directly to the —O—C— moiety of the parent compound with l, q and p being 0. In some embodiments, the organometallic compound may be connected by a C$_1$- to C$_4$-alkyl to the —O—C— moiety of the parent compound with l and q being 0 and p being an integer of 1 to 4, in particular p being 1. In some embodiments, the organometallic compound may be connected to the —O—C— moiety of the parent compound by a —C(=O)— or C(=S)— group, in particular by a —C(=O)— group, with l being 1, q and p being 0. In some embodiments, the organometallic compound may be connected to the —O—C— moiety of the parent compound by a —C(=O)— or C(=S)— group, in particular by a —C(=O)— group, with l being 1, q being 0 and p being an integer of 1 to 4, in particular p being 1. In some embodiments, the organometallic compound may be connected to the —O—C— moiety of the parent compound by a —C(=O)— or C(=S)— group, in particular by a —C(=O)— group, with l being 1, p being 0 and q being an integer of 1 to 4, in particular q being 1.

In some embodiments, n of R$^1_n$ is 1 or 2, and each R$^1$ independently from any other R$^1$ is —C(=O)OR$^2$, —C(=O)NR$^2_2$, —C(=O)SR$^2$, —C(=S)OR$^2$ —C(NH)NR$^2_2$, CN$_4$H$_2$, —NR$^2_2$, —C(=O)R$^2$, —C(=S)R$^2$, —OR$^2$, —SR$^2$, —CF$_3$, —OCF$_3$, —SCF$_3$, —SOCF$_3$, —SO$_2$CF$_3$, —CN, —NO$_2$, —F, —Cl, —Br or —I, with each R$^2$ independently from any other R$^2$ being hydrogen, CH$_3$, C$_2$H$_5$, C$_3$H$_7$ or C$_4$H$_9$, in particular with each R$^2$ being hydrogen.

In some embodiments, n of R$^1_n$ is 1 or 2 and each R$^1$ independently from any other R$^1$ is —CN, —CF$_3$, —OCF$_3$, —SCF$_3$, —SOCF$_3$, —SO$_2$CF$_3$, —F, —Cl, —Br or —I. In some embodiments, n of R$^1_n$ is 1 or 2 and each R$^1$ independently from any other R$^1$ is —CN, —CF$_3$, —SCF$_3$, —SOCF$_3$ or —SO$_2$CF$_3$. In some embodiments, n of R$^1_n$ is 1 or 2 and each R$^1$ independently from any other R$^1$ is —F, —Cl, —Br or —I.

In some embodiments, n of R$^1_n$ is 2 and each R$^1$ independently from any other R$^1$ is —CN, —CF$_3$, —OCF$_3$, —F, —Cl, —Br or —I. In some embodiments, n of R$^1_n$ is 2 and each R$^1$ independently from any other R$^1$ is —CN or —CF$_3$.

In some embodiments, n of R$^1_n$ is 2 and one of the two R$^1$ is in ortho and the other R$^1$ is in meta position to the attachment position of the benzene moiety. In some embodiments, n of R$^1_n$ is 2, each R$^1$ independently from any other R$^1$ is —CN, —CF$_3$, —OCF$_3$, —SCF$_3$, —SOCF$_3$, —SO$_2$CF$_3$, —F, —Cl, —Br or —I, in particular each R$^1$ independently from any other R$^1$ is —CN, —CF$_3$, —OCF$_3$, —F, —Cl or —Br, and one of the two $R^1$ is in ortho and the other $R^1$ is in meta position to the attachment position of the benzene moiety.

In some embodiments, n of $R^1_n$ is 2, each $R^1$ independently from any other $R^1$ is —CN or —$CF_3$ and one of the two $R^1$ is in ortho and the other $R^1$ is in meta position to the attachment position of the benzene moiety. In some embodiments, n of $R^1_n$ is 2 and one of the two $R^1$ is —$CF_3$ in ortho and the other $R^1$ is —CN in meta position to the attachment position of the benzene moiety.

In some embodiments, n of $R^1_n$ is 1 and $R^1$ is —CN, —$CF_3$, —$OCF_3$, —$SCF_3$, —$SOCF_3$, —$SO_2CF_3$, —F, —Cl, —Br or —I. In some embodiments, n of $R^1_n$ is 1 and $R^1$ is —$SCF_3$, —$SOCF_3$ or —$SO_2CF_3$, in particular $R^1$ is —$SCF_3$.

In some embodiments, n of $R^1_n$ is 1 and $R^1$ is in para position to the attachment position of the benzene moiety. In some embodiments, n of $R^1_n$ is 1, $R^1$ is —CN, —$CF_3$, —$OCF_3$, —$SCF_3$, —$SOCF_3$, —$SO_2CF_3$, —F, —Cl, —Br or —I, in particular $R^1$ is —$SCF_3$, —$SOCF_3$, —$SO_2CF_3$, —F, —Cl or —Br, and $R^1$ is in para position to the attachment position of the benzene moiety.

In some embodiments, n of $R^1_n$ is 1 and $R^1$ is —$SCF_3$, —$SOCF_3$, —$SO_2CF_3$ and $R^1$ is in para position to the attachment position of the benzene moiety. In some embodiments, n of $R^1_n$ is 1, $R^1$ is —$SCF_3$ and $R^1$ is in para position to the attachment position of the benzene moiety.

In some embodiments, l of $F_l$ is 0, wherein q of $K_q$ and p of $K_p$ are 0.

In some embodiments, $F_l$ is —C(=O)— or —C(=S), with l being 1, wherein q of $K_q$ and p of $K_p$ are 0. In some embodiments, $F_l$ is —C(=O)—, with l being 1, wherein q of $K_q$ and p of $K_p$ are 0. In some embodiments, $F_l$ is —C(=O)—, with l being 1, q of $K_q$ is 0 and $K_p$ is $C_1$-alkyl. In some embodiments, $F_l$ is —C(=O)—, with l being 1, q of $K_q$ is 0 and $K_p$ is $C_2$-alkyl.

In some embodiments, l of $F_l$ is 0, q of $K_q$ is 0 and $K_p$ is $C_1$-alkyl.

In some embodiments, l of $F_l$ is 0, q of $K_q$ is 0 and $K_p$ is $C_2$-alkyl.

In some embodiments, $F_f$ is —C(=O)—, with l being 1, p of $K_p$ is 0 and $K_q$ is $C_1$-alkyl. In some embodiments, $F_l$ is —C(=O)—, with l being 1, p of $K_p$ is 0 and $K_q$ is $C_2$-alkyl.

In some embodiments, $F_l$ is —C(=O)—, with l being 1, $K_p$ is $C_1$-alkyl and $K_q$ is $C_1$-alkyl or $C_2$-alkyl. In some embodiments, $F_l$ is —C(=O)—, with l being 1, $K_p$ is $C_2$-alkyl and $K_q$ is $C_1$-alkyl or $C_2$-alkyl.

In some embodiments, l of $F_l$ is 0, q of $K_q$ is 0, p of $K_p$ is 0 and n of $R^1_n$ is 2. In some embodiments, l of $F_l$ is 0, q of $K_q$ is 0, p of $K_p$ is 0, n of $R^1_n$ is 2 and one of the two $R^1$ is in ortho and the other $R^1$ is in meta position to the attachment position of the benzene moiety. In some embodiments, l of $F_l$ is 0, q of $K_q$ is 0, p of $K_p$ is 0, n of $R^1_n$ is 2 and one of the two $R^1$ is —$CF_3$ in ortho and the other $R^1$ is —CN in meta position to the attachment position of the benzene moiety. In some embodiments, l of $F_l$ is 0, q of $K_q$ is 0, $K_p$ is $C_1$- or $C_2$-alkyl, n of $R^1_n$ is 2 and one of the two $R^1$ is in ortho and the other $R^1$ is in meta position to the attachment position of the benzene moiety. In some embodiments, l of $F_l$ is 0, q of $K_q$ is 0, $K_p$ is $C_1$- or $C_2$-alkyl, n of $R^1_n$ is 2 and one of the two $R^1$ is —$CF_3$ in ortho and the other $R^1$ is —CN in meta position to the attachment position of the benzene moiety.

In some embodiments, l of $F_l$ is 0, q of $K_q$ is 0, p of $K_p$ is 0 and n of $R^1_n$ is 1. In some embodiments, l of $F_l$ is 0, q of $K_q$ is 0, p of $K_p$ is 0, n of $R^1_n$ is 1 and $R^1$ is in para position to the attachment position of the benzene moiety. In some embodiments, l of $F_l$ is 0, q of $K_q$ is 0, p of $K_p$ is 0, n of $R^1_n$ is 1 and $R^1$ is —$SCF_3$, —$SOCF_3$ or —$SO_2CF_3$ in para position to the attachment position of the benzene moiety. In some embodiments, l of $F_l$ is 0, q of $K_q$ is 0, p of $K_p$ is 0, n of $R^1_n$ is 1 and $R^1$ is —$SCF_3$ in para position to the attachment position of the benzene moiety. In some embodiments, l of $F_l$ is 0, q of $K_q$ is 0, $K_p$ is $C_1$- or $C_2$-alkyl, n of $R^1_n$ is 1 and $R^1$ is in para position to the attachment position of the benzene moiety. In some embodiments, l of $F_l$ is 0, q of $K_q$ is 0, $K_p$ is $C_1$- or $C_2$-alkyl, n of $R^1_n$ is 1 and $R^1$ is —$SCF_3$, —$SOCF_3$ or —$SO_2CF_3$ in para position to the attachment position of the benzene moiety. In some embodiments, l of $F_l$ is 0, q of $K_q$ is 0, $K_p$ is $C_1$- or $C_2$-alkyl, n of $R^1_n$ is 1 and $R^1$ is —$SCF_3$ in para position to the attachment position of the benzene moiety.

In some embodiments $F_l$ is —C(=O)— or —C(=S)—, with l being 1, q of $K_q$ is 0, p of $K_p$ is 0 and n of $R^1_n$ is 2. In some embodiments $F_l$ is —C(=O)—, with l being 1, q of $K_q$ is 0, p of $K_p$ is 0 and n of $R^1_n$ is 2. In some embodiments, $F_l$ is —C(=O)—, with l being 1, q of $K_q$ is 0, p of $K_p$ is 0, n of $R^1_n$ is 2 and one of the two $R^1$ is in ortho and the other $R^1$ is in meta position to the attachment position of the benzene moiety. In some embodiments, $F_l$ is —C(=O)—, with l being 1, q of $K_q$ is 0, p of $K_p$ is 0, n of $R^1_n$ is 2 and one of the two $R^1$ is —$CF_3$ in ortho and the other $R^1_n$ is —CN in meta position to the attachment position of the benzene moiety.

In some embodiments, $F_l$ is —C(=O)— or —C(=S)—, with l being 1, q of $K_q$ is 0, p of $K_p$ is 0 and n of $R^1_n$ is 1. In some embodiments, $F_l$ is —C(=O)—, with l being 1, q of $K_q$ is 0, p of $K_p$ is 0 and n of $R^1_n$ is 1. In some embodiments, $F_l$ is —C(=O)—, with l being 1, q of $K_q$ is 0, p of $K_p$ is 0, n of $R^1_n$ is 1 and $R^1$ is in para position to the attachment position of the benzene moiety. In some embodiments, $F_l$ is —C(=O)—, with l being 1, q of $K_q$ is 0, p of $K_p$ is 0, n of $R^1_n$ is 1 and $R^1$ is —$SCF_3$, —$SOCF_3$ or —$SO_2CF_3$ in para position to the attachment position of the benzene moiety. In some embodiments, $F_l$ is —C(=O)—, with l being 1, q of $K_q$ is 0, p of $K_p$ is 0 and n of $R^1_n$ is 1 and $R^1$ is —$SCF_3$ in para position to the attachment position of the benzene moiety.

In some embodiments, $F_l$ is —C(=O)—, with l being 1, q of $K_q$ is 0, $K_p$ is $C_1$- or $C_2$-alkyl, n of $R^1_n$ is 2. In some embodiments, $F_l$ is —C(=O)—, with l being 1, q of $K_q$ is 0, $K_p$ is $C_1$- or $C_2$-alkyl, n of $R^1_n$ is 2 and one of the two $R^1$ is in ortho and the other $R^1$ is in meta position to the attachment position of the benzene moiety. In some embodiments, $F_l$ is —C(=O)—, with l being 1, q of $K_q$ is 0, $K_p$ is $C_1$- or $C_2$-alkyl, n of $R^1_n$ is 2 and one of the two $R^1$ is —$CF_3$ in ortho and the other $R^1$ is —CN in meta position to the attachment position of the benzene moiety.

In some embodiments, $F_l$ is —C(=O)—, with l being 1, q of $K_q$ is 0, $K_p$ is $C_1$- or $C_2$-alkyl, n of $R^1_n$ is 1. In some embodiments, $F_l$ is —C(=O)—, with l being 1, q of $K_q$ is 0, $K_p$ is $C_1$- or $C_2$-alkyl, n of $R^1_n$ is 1 and $R^1$ is in para position to the attachment position of the benzene moiety. In some embodiments, $F_l$ is —C(=O)—, with l being 1, q of $K_q$ is 0, $K_p$ is $C_1$-alkyl, n of $R^1_n$ is 1 and $R^1$ is —$SCF_3$, —$SOCF_3$ or —$SO_2CF_3$ in para position to the attachment position of the benzene moiety. In some embodiments, $F_l$ is —C(=O)—, with l being 1, q of $K_q$ is 0, $K_p$ is $C_1$-alkyl, n of $R^1_n$ is 1 and $R^1$ is —$SCF_3$ in para position to the attachment position of the benzene moiety. In some embodiments, $F_l$ is —C(=O)—, with l being 1, q of $K_q$ is 0, $K_p$ is $C_2$-alkyl, n of $R^1_n$ is 1 and $R^1$ is —$SCF_3$, —$SOCF_3$ or —$SO_2CF_3$ in para position to the attachment position of the benzene moiety. In some embodiments, $F_l$ is —C(=O)—, with l being 1, q of $K_q$ is 0, $K_p$ is $C_2$-alkyl, n of $R^1_n$ is 1 and $R^1$ is —$SCF_3$ in para position to the attachment position of the benzene moiety.

In some embodiments, OM is a metal sandwich complex, wherein each of the two sandwich ligands is selected independently from a five-membered or six-membered aryl group or a five-membered or six-membered heteroaryl group. In some embodiments, OM is a metal sandwich complex, wherein both sandwich ligands are the same and are selected from a five-membered or six-membered aryl group or a five-membered or six-membered heteroaryl group. In some embodiments, OM is a metal sandwich complex, wherein at least one of the two ligands is selected from a five-membered or six-membered aryl group, wherein the other is selected from a five-membered or six-membered heteroaryl group. In some embodiments, OM is a substituted or unsubstituted metallocene, wherein each of two ligands is selected independently from a five-membered aryl group (cp-ligand) or a five-membered heteroaryl group (hetero cp-ligand). The metal sandwich complex may be connected to the parent molecule by any atom of one of the two sandwich ligands.

In some embodiments, OM is a metal sandwich complex of the general formula (2a),

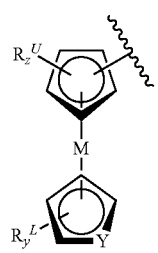

(2a)

wherein M is a metal selected from the group of Fe, Ru, Co, Ni, Cr, Os or Mn, and
Y is C or N, and
z of $R_z^U$ is 0, 1, 2, 3 or 4, and y of $R_y^L$ is 0, 1, 2, 3, 4 or 5 and
each $R^L$ and each $R^U$ are independently from any other $R^L$ and $R^U$ selected from
an unsubstituted or substituted $C_1$-$C_{10}$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy,
an unsubstituted or substituted $C_6$-$C_{14}$ aryl,
an unsubstituted or substituted 5- to 10-membered heteroaryl, wherein 1 to 4 ring atoms are independently selected from nitrogen, oxygen or sulfur,
an unsubstituted or substituted 5- to 10-membered heteroalicyclic ring, wherein 1 to 3 ring atoms are independently selected from nitrogen, oxygen or sulfur,
—$OR^3$, —$SR^3$, —$C(O)R^3$, —$C(S)R^3$, —$C(O)OR^3$, —$C(S)OR^3$, —$C(O)SR^3$, —$C(O)NR^3R^4$, —$NR^3R^4$, —$S(O)_2R^3$, —$S(O)_2OR^3$ and —$S(O)_2NR^3R^4$,
wherein
$R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, z of $R_z^U$ is 0, 1, 2, 3 or 4, and y of $R_y^L$ is 0, 1, 2, 3, 4 or 5, and each $R^L$ and each $R^U$ are independently from any other $R^L$ and $R^U$ selected from —$OR^3$, —$SR^3$, —$C(O)R^3$, —$C(S)R^3$, —$C(O)OR^3$, —$C(S)OR^3$, —$C(O)SR^3$, —$C(O)NR^3R^4$, —$NR^3R^4$, —$S(O)_2R^3$, —$S(O)_2OR^3$ and —$S(O)_2NR^3R^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, M of the general formula 2a is Fe, Ru or Co.

In some embodiments, M of the general formula 2a is Fe.

In some embodiments, Y is C.

In some embodiments, M of the general formula 2a is Fe and Y is C.

In some embodiments, Y is C, and z of $R_z^U$ is 0, 1, 2, 3 or 4, y of $R_y^L$ is 0, 1, 2, 3, 4 or 5, and each $R^L$ and each $R^U$ are independently from any other $R^L$ and $R^U$ selected from —$OR^3$, —$SR^3$, —$C(O)R^3$, —$C(S)R^3$, —$C(O)OR^3$, —$C(S)OR^3$, —$C(O)SR^3$, —$C(O)NR^3R^4$, —$NR^3R^4$, —$S(O)_2R^3$, —$S(O)_2OR^3$ and —$S(O)_2NR^3R^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, M of the general formula 2a is a metal selected from the group of Fe, Ru, Co, Ni, Cr, Os or Mn, in particular M is Fe, Y is C or N, z of $R_z^U$ is 1, y of $R_y^L$ is 1, and wherein $R^U$ and $R^L$ are selected independently from any other $R^U$ and $R^L$ from —$OR^3$, —$SR^3$, —$C(O)R^3$, —$C(S)R^3$ —$C(O)OR^3$, —$C(S)OR^3$, —$C(O)SR^3$ —$C(O)NR^3R^4$, —$NR^3R^4$, —$S(O)_2R^3$, —$S(O)_2OR^3$ and —$S(O)_2NR^3R^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, M of the general formula 2a is a metal selected from the group of Fe, Ru, Co, Ni, Cr, Os or Mn, in particular M is Fe, Y is C or N, and z of $R_z^U$ is 0, y of $R_y^L$ is 1, and wherein $R^L$ is selected from —$OR^3$, —$SR^3$, —$C(O)R^3$, —$C(S)R^3$ —$C(O)OR^3$, —$C(S)OR^3$, —$C(O)SR^3$ —$C(O)NR^3R^4$, —$NR^3R^4$, —$S(O)_2R^3$, —$S(O)_2OR^3$ and —$S(O)_2NR^3R^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, Y is N, z of $R_z^U$ is 0 and y of $R_y^L$ is 0. In some embodiments, Y is N, z of $R_z^U$ is 0, y of $R_y^L$ is 0, and M of the general formula 2a is selected from the group of Fe, Ru or Co.

In some embodiments, Y is C, z of $R_z^U$ is 0 and y of $R_y^L$ is 0. In some embodiments, Y is C, z of $R_z^U$ is 0, y of $R_y^L$ is 0, and M of the general formula 2a is selected from the group of Fe, Ru or Co.

In some embodiments, l of $F_l$ is 0, q of $K_1$ is 0, p of $K_p$ is 0, Y is C, z of $R_z^U$ is 0, y of $R_y^L$ is 0, and M of the general formula 2a is selected from the group of Fe, Ru, Co, Ni, Cr, Os or Mn.

In some embodiments, M of the general formula 2a is selected from the group of Fe, Ru, Co, Ni, Cr, Os or Mn, in particular M is selected from Fe, Ru or Co, Y is C, z of $R_z^U$ is 0, y of $R_y^L$ is 0 and
$F_l$ is —$C(=O)$— or —$C(=S)$, with l being 1, q of $K_q$ is 0, p of $K_p$ is 0;
$F_l$ is —$C(=O)$—, with l being 1, q of $K_q$ is 0, p of $K_p$ is 0;
$F_l$ is —$C(=O)$— or —$C(=S)$, with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, p of $K_p$ is $C_1$- or $C_2$-alkyl, $K_q$ is $C_1$- or $C_2$-alkyl;

$F_l$ is —C(=O)— with l being 1, q of $K_q$ is 0, p of $K_p$ is 0, n of $R^1{}_n$ is 2;

$F_l$ is —C(=O)—, with l being 1, q of $K_q$ is 0, p of $K_p$ is 0, n of $R^1{}_n$ is 2, one of the two $R^1$ is in ortho and the other $R^1$ is in meta position to the attachment position of the benzene moiety $F_l$ is —C(=O)—, with l being 1, q of $K_q$ is 0, p of $K_p$ is 0, n of $R^1{}_n$ is 2, one of the two $R^1$ is —$CF_3$ in ortho and the other $R^1$ is —CN in meta position to the attachment position of the benzene moiety;

$F_l$ is —C(=O)—, with l being 1, q of $K_q$ is 0, p of $K_p$ is 0, n of $R^1{}_n$ is 1;

$F_l$ is —C(=O)—, with l being 1, q of $K_q$ is 0, p of $K_p$ is 0, n of $R^1{}_n$ is 1; $R^1$ is in para position to the attachment position of the benzene moiety;

$F_l$ is —C(=O)—, with l being 1, q of $K_q$ is 0, p of $K_p$ is 0, n of $R^1{}_n$ is 1; $R^1$ is —$SCF_3$, —$SOCF_3$, —$SO_2CF_3$ in para position to the attachment position of the benzene moiety;

$F_l$ is —C(=O)—, with l being 1, q of $K_q$ is 0, p of $K_p$ is 0, n of $R^1{}_n$ is 1 and $R^1$ is —$SCF_3$ in para position to the attachment position of the benzene moiety;

$F_l$ is —C(=O)—, with l being 1, q of $K_q$ is 0, $K_p$ is $C_1$- or $C_2$-alkyl, n of $R^1{}_n$ is 2, one of the two $R^1$ is —$CF_3$ in ortho and the other $R^1$ is —CN in meta position to the attachment position of the benzene moiety;

$F_l$ is —C(=O)—, with l being 1, q of $K_q$ is 0, $K_p$ is $C_1$-alkyl, n of $R^1{}_n$ is 1, $R^1$ is —$SCF_3$, —$SOCF_3$, —$SO_2CF_3$ in para position to the attachment position of the benzene moiety;

$F_l$ is —C(=O)—, with l being 1, q of $K_q$ is 0, $K_p$ is $C_1$-alkyl, n of $R^1{}_n$ is 1, $R^1$ is —$SCF_3$ in para position to the attachment position of the benzene moiety;

$F_l$ is with l being 1, q of $K_q$ is 0, $K_p$ is $C_2$-alkyl, n of $R^1{}_n$ is 1, $R^1$ is —$SCF_3$, —$SOCF_3$, —$SO_2CF_3$ in para position to the attachment position of the benzene moiety;

$F_l$ is —C(=O)—, with l being 1, q of $K_q$ is 0, $K_p$ is $C_2$-alkyl, n of $R^1{}_n$ is 1 and $R^1$ is —$SCF_3$ in para position to the attachment position of the benzene moiety;

l of $F_l$ is 0, q of $K_q$ is 0, p of $K_p$ is 0;

l of $F_l$ is 0, q of $K_q$ is 0, p of $K_p$ is 0, n of $R^1{}_n$ is 2;

l of $F_l$ is 0, g of $K_q$ is 0, p of $K_p$ is 0, n of $R^1{}_n$ is 2, one of the two $R^1$ is in ortho and the other $R^1$ is in meta position to the attachment position of the benzene moiety;

l of $F_l$ is 0, q of $K_q$ is 0, p of $K_p$ is 0, n of $R^1{}_n$ is 2, one of the two $R^1$ is —$CF_3$ in ortho and the other $R^1$ is —CN in meta position to the attachment position of the benzene moiety;

l of $F_f$ is 0, q of $K_q$ is 0, p of $K_p$ is 0, n of $R^1{}_n$ is 1;

l of $F_l$ is 0, q of $K_q$ is 0, p of $K_p$ is 0, n of $R^1{}_n$ is 1 and $R^1$ is in para position to the attachment position of the benzene moiety;

l of $F_l$ is 0, q of $K_q$ is 0, p of $K_p$ is 0, n of R/n is 1 and $R^1$ is —$SCF_3$, —$SOCF_3$, —$SO_2CF_3$ in para position to the attachment position of the benzene moiety;

l of $F_l$ is 0, q of $K_q$ is 0, p of $K_p$ is 0, n of $R^1{}_n$ is 1 and $R^1$ is —$SCF_3$ in para position to the attachment position of the benzene moiety;

l of $F_l$ is 0, q of $K_q$ is 0, $K_p$ is $C_1$- or $C_2$-alkyl;

l of $F_l$ is 0, p of $K_p$ is 0, $K_q$ is $C_1$- or $C_2$-alkyl;

l of $F_l$ is 0, p of $K_p$ is 0, $K_q$ is $C_1$- or $C_2$-alkyl, n of $R^1{}_n$ is 1 or 2;

$F_l$ is 0, q of $K_q$ is 0, $K_p$ is $C_1$- or $C_2$-alkyl, n of $R^1{}_n$ is 2;

$F_l$ is 0, q of $K_q$ is 0, $K_p$ is $C_1$- or $C_2$-alkyl, n of $R^1{}_n$ is 2, one of the two $R^1$ is in ortho and the other $R^1$ is in meta position to the attachment position of the benzene moiety;

$F_l$ is 0, q of $K_q$ is 0, $K_p$ is $C_1$- or $C_2$-alkyl, n of $R^1{}_n$ is 2, one of the two $R^1$ is —$CF_3$ in ortho and the other $R^1$ is —CN in meta position to the attachment position of the benzene moiety;

$F_l$ is 0, q of $K_q$ is 0, $K_p$ is $C_1$- or $C_2$-alkyl, n of $R^1{}_n$ is 1;

$F_l$ is 0, q of $K_q$ is 0, $K_p$ is $C_1$- or $C_2$-alkyl, n of $R^1{}_n$ is 1 and $R^1$ in para position to the attachment position of the benzene moiety;

$F_l$ is 0, q of $K_q$ is 0, $K_p$ is $C_1$- or $C_2$-alkyl, n of $R^1{}_n$ is 1 and $R^1$ is —$SCF_3$, —$SOCF_3$, —$SO_2CF_3$ in para position to the attachment position of the benzene moiety;

l of $F_l$ is 0, q of $K_q$ is 0, $K_p$ is $C_1$- or $C_2$-alkyl, n of $R^1{}_n$ is 1 and $R^1$ is —$SCF_3$ in para position to the attachment position of the benzene moiety;

wherein—if not stated otherwise—each of the above mentioned $R^1{}_n$ is selected independently from any possible other $R^1{}_n$ from the group —C(=O)$OR^2$, —C(=O)$NR^2{}_2$, —C(=O)$SR^2$, —C(=S)$OR^2$, —C(NH)$NR^2{}_2$, $CN_4H_2$, —$NR^2{}_2$, —C(=O)$R^2$, —C(=S)$R^2$, —$OR^2$, —$SR^2$, —$CF_3$, —$OCF_3$, —$SCF_3$, —$SOCF_3$, —$SO_2CF_3$, —CN, —$NO_2$, —F, —Cl, —Br or —I.

In some embodiments, M of the general formula 2a is Fe, Y is C, z of $R_z{}^U$ is 0, y of $R_y{}^L$ is 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, p of $K_r$ is $C_1$- or $C_2$-alkyl, $K_q$ is $C_1$- or $C_2$-alkyl;

$F_l$ is —C(=O)— with l being 1, q of $K_q$ is 0, p of $K_p$ is 0, n of $R^1{}_n$ is 2;

$F_l$ is —C(=O)—, with l being 1, q of $K_q$ is 0, p of $K_p$ is 0, n of $R^1{}_n$ is 2, one of the two $R^1$ is in ortho and the other $R^1$ is in meta position to the attachment position of the benzene moiety $F_l$ is —C(=O)—, with l being 1, q of $K_q$ is 0, p of $K_p$ is 0, n of $R^1{}_n$ is 2, one of the two $R^1$ is —$CF_3$ in ortho and the other $R^1$ is —CN in meta position to the attachment position of the benzene moiety;

$F_l$ is —C(=O)—, with l being 1, q of $K_q$ is 0, p of $K_p$ is 0, n of $R^1{}_n$ is 1;

$F_l$ is —C(=O)—, with l being 1, q of $K_q$ is 0, p of $K_p$ is 0, n of $R^1{}_n$ is 1; $R^1$ is in para position to the attachment position of the benzene moiety;

$F_l$ is —C(=O)—, with l being 1, q of $K_q$ is 0, p of $K_p$ is 0, n of $R^1{}_n$ is 1; $R^1$ is —$SCF_3$, —$SOCF_3$, —$SO_2CF_3$ in para position to the attachment position of the benzene moiety;

$F_l$ is —C(=O)—, with l being 1, q of $K_q$ is 0, p of $K_p$ is 0, n of $R^1{}_n$ is 1 and $R^1$ is —$SCF_3$ in para position to the attachment position of the benzene moiety;

$F_l$ is —C(=O)—, with l being 1, q of $K_q$ is 0, $K_p$ is $C_1$- or $C_2$-alkyl, n of $R^1{}_n$ is 2, one of the two $R^1$ is —$CF_3$ in ortho and the other $R^1$ is —CN in meta position to the attachment position of the benzene moiety;

$F_l$ is —C(=O)—, with l being 1, q of $K_q$ is 0, $K_p$ is n of $R^1_n$ is 1, $R^1$ is —SCF$_3$, —SOCF$_3$, —SO$_2$CF$_3$ in para position to the attachment position of the benzene moiety;

$F_l$ is —C(=O)—, with l being 1, q of $K_q$ is 0, $K_p$ is $C_1$-alkyl, n of $R^1_n$ is 1, $R^1$ is —SCF$_3$ in para position to the attachment position of the benzene moiety;

$F_l$ is —C(=O)—, with l being 1, q of $K_q$ is 0, $K_p$ is $C_2$-alkyl, n of $R^1_n$ is 1, $R^1$ is —SCF$_3$, —SOCF$_3$, —SO$_2$CF$_3$ in para position to the attachment position of the benzene moiety;

$F_l$ is —C(=O)—, with l being 1, q of $K_q$ is 0, $K_p$ is $C_2$-alkyl, n of $R^1_n$ is 1 and R' is —SCF$_3$ in para position to the attachment position of the benzene moiety;

l of $F_l$ is 0, q of $K_q$ is 0, p of $K_p$ is 0;

l of $F_l$ is 0, q of $K_q$ is 0, p of $K_p$ is 0, n of $R^1_n$ is 2;

l of $F_l$ is 0, q of $K_q$ is 0, p of $K_p$ is 0, n of $R^1_n$ is 2, one of the two $R^1$ is in ortho and the other $R^1$ is in meta position to the attachment position of the benzene moiety;

l of $F_l$ is 0, q of $K_q$ is 0, p of $K_p$ is 0, n of $R^1_n$ is 2, one of the two $R^1$ is —CF$_3$ in ortho and the other $R^1$ is —CN in meta position to the attachment position of the benzene moiety;

l of $F_l$ is 0, q of $K_q$ is 0, p of $K_p$ is 0, n of $R^1_n$ is 1;

l of $F_l$ is 0, q of $K_q$ is 0, p of $K_p$ is 0, n of $R^1_n$ is 1 and $R^1$ is in para position to the attachment position of the benzene moiety;

l of $F_l$ is 0, q of $K_q$ is 0, p of $K_p$ is 0, n of $R^1_n$ is 1 and $R^1$ is —SCF$_3$, —SOCF$_3$, —SO$_2$CF$_3$ in para position to the attachment position of the benzene moiety;

l of $F_l$ is 0, q of $K_q$ is 0, p of $K_p$ is 0, n of $R^1_n$ is 1 and $R^1$ is —SCF$_3$ in para position to the attachment position of the benzene moiety;

l of $F_l$ is 0, q of $K_q$ is 0, $K_p$ is $C_1$- or $C_2$-alkyl;

l of $F_l$ is 0, p of $K_p$ is 0, $K_q$ is $C_1$- or $C_2$-alkyl;

l of $F_l$ is 0, p of $K_p$ is 0, $K_q$ is $C_1$- or $C_2$-alkyl, n of $R^1_n$ is 1 or 2;

$F_l$ is 0, q of $K_q$ is 0, $K_p$ is $C_1$- or $C_2$-alkyl, n of $R^1_n$ is 2;

$F_l$ is 0, q of $K_q$ is 0, $K_p$ is $C_1$- or $C_2$-alkyl, n of $R^1_n$ is 2, one of the two $R^1$ is in ortho and the other $R^1$ is in meta position to the attachment position of the benzene moiety;

$F_l$ is 0, q of $K_q$ is 0, $K_p$ is $C_1$- or $C_2$-alkyl, n of $R^1_n$ is 2, one of the two $R^1$ is —CF$_3$ in ortho and the other $R^1$ is —CN in meta position to the attachment position of the benzene moiety;

$F_l$ is 0, q of $K_q$ is 0, $K_p$ is $C_1$- or $C_2$-alkyl, n of $R^1_n$ is 1;

$F_l$ is 0, q of $K_q$ is 0, $K_p$ is $C_1$- or $C_2$-alkyl, n of $R^1_n$ is 1 and $R^1$ in para position to the attachment position of the benzene moiety;

$F_l$ is 0, q of $K_q$ is 0, $K_p$ is $C_1$- or $C_2$-alkyl, n of $R^1_n$ is 1 and $R^1$ is —SCF$_3$, —SOCF$_3$, —SO$_2$CF$_3$ in para position to the attachment position of the benzene moiety;

l of $F_l$ is 0, q of $K_q$ is 0, $K_p$ is $C_1$- or $C_2$-alkyl, n of $R^1_n$ is 1 and $R^1$ is —SCF$_3$ in para position to the attachment position of the benzene moiety;

wherein each of the above mentioned $R^1_n$ is selected independently from any possible other $R^1_n$—if not stated otherwise—from the group —C(=O)OR$^2$, —C(=O)NR$^2_2$, —C(=O)SR$^2$, —C(=S)OR$^2$, —C(NH)NR$^2_2$, CN$_4$H$_2$, —NR$^2_2$, —C(=O)R$^2$, —C(=S)R$^2$, —OR$^2$, —SR$^2$, —CF$_3$, —OCF$_3$, —SCF$_3$, —SOCF$_3$, —SO$_2$CF$_3$, —CN, —NO$_2$, —F, —Cl, —Br or —I.

In some embodiments, OM is a half metal sandwich complex of the general formula (2b),

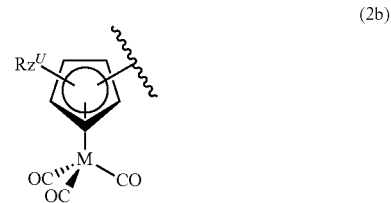

(2b)

wherein M is a metal selected from the group of Mn, Re or Tc, and z of $R_z^U$ is 0, 1, 2, 3 or 4, and each Ru is independently from any other $R^U$ selected from
an unsubstituted or substituted $C_1$-$C_{10}$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy, an unsubstituted or substituted $C_6$-$C_{14}$ aryl, an unsubstituted or substituted 5- to 10-membered heteroaryl, wherein 1 to 4 ring atoms are independently selected from nitrogen, oxygen or sulfur, an unsubstituted or substituted 5- to 10-membered heteroalicyclic ring, wherein 1 to 3 ring atoms are independently nitrogen, oxygen or sulfur, —OR$^3$, —SR$^3$, —C(O)R$^3$, —C(S)R$^3$, —C(O)OR$^3$, —C(S)OR$^3$, —C(O)SR$^3$, —C(O)NR$^3$R$^4$, —NR$^3$R$^4$, —S(O)$_2$R$^3$, —S(O)$_2$OR$^3$, and —S(O)$_2$NR$^3$R$^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, z of $R_z^U$ of the general formula 2b is 0, 1, 2, 3 or 4, and each $R^U$ is independently from any other $R^U$ selected from —OR$^3$, —SR$^3$, —C(O)R$^3$, —C(S)R$^3$, —C(O)OR$^3$, —C(S)OR$^3$, —C(O)SR$^3$, —C(O)NR$^3$R$^4$, —NR$^3$R$^4$, —S(O)$_2$R$^3$, —S(O)$_2$OR$^3$, and —S(O)$_2$NR$^3$R$^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, z of $R_z^U$ of the general formula 2b is 1, and $R^U$ is selected from —OR$^3$, —SR$^3$, —C(O)R$^3$, —C(S)R$^3$ —C(O)OR$^3$, —C(S)OR$^3$, —C(O)SR$^3$ —C(O)NR$^3$R$^4$, —NR$^3$R$^4$, —S(O)$_2$R$^3$, —S(O)$_2$OR$^3$ and —S(O)$_2$NR$^3$R$^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, z of $R_z^U$ of the general formula 2b is 0

In some embodiments, M of the general formula 2b is Mn, Re or Tc, z of $R_z^U$ is 0, and $F_l$ is —C(=O)— or —C(=S), with l being 1, q of $K_q$ is 0, p of $K_p$ is 0;

$F_l$ is —C(=O)—, with l being 1, q of $K_q$ is 0, p of $K_p$ is 0;

$F_l$ is —C(=O)— or —C(=S), with l being 1, q of $K_q$ is 0, $K_p$ is $C_1$- or $C_2$-alkyl;

$F_l$ is —C(=O)—, with l being 1, q of $K_q$ is 0, $K_p$ is $C_1$- or $C_2$-alkyl;

$F_l$ is —C(=O)—, with l being 1, p of $K_p$ is 0, $K_q$ is $C_1$- or $C_2$-alkyl;

$F_l$ is —C(=O)—, with l being 1, p of $K_p$ is $C_1$- or $C_2$-alkyl, $K_q$ is $C_1$- or $C_2$-alkyl;

$F_l$ is —C(=O)— with l being 1, q of $K_q$ is 0, p of $K_p$ is 0, n of $R^1{}_n$ is 2;

$F_l$ is —C(=O)—, with l being 1, q of $K_q$ is 0, p of $K_p$ is 0, n of $R^1{}_n$ is 2, one of the two $R^1$ is in ortho and the other $R^1$ is in meta position to the attachment position of the benzene moiety $F_l$ is —C(=O)—, with l being 1, q of $K_q$ is 0, p of $K_p$ is 0, n of $R^1{}_n$ is 2, one of the two $R^1$ is —$CF_3$ in ortho and the other $R^1$ is —CN in meta position to the attachment position of the benzene moiety;

$F_l$ is —C(=O)—, with l being 1, q of $K_q$ is 0, p of $K_p$ is 0, n of $R^1{}_n$ is 1;

$F_l$ is —C(=O)—, with l being 1, q of $K_q$ is 0, p of $K_p$ is 0, n of $R^1{}_n$ is 1; $R^1$ is in para position to the attachment position of the benzene moiety;

$F_l$ is —C(=O)—, with l being 1, q of $K_q$ is 0, p of $K_p$ is 0, n of $R^1{}_n$ is 1; R' is —$SCF_3$, —$SOCF_3$, —$SO_2CF_3$ in para position to the attachment position of the benzene moiety;

$F_l$ is —C(=O)—, with l being 1, q of $K_q$ is 0, p of $K_p$ is 0, n of $R^1{}_n$ is 1 and $R^1$ is —$SCF_3$ in para position to the attachment position of the benzene moiety;

$F_l$ is —C(=O)—, with l being 1, q of $K_q$ is 0, $K_p$ is $C_1$- or $C_2$-alkyl, n of $R^1{}_n$ is 2, one of the two $R^1$ is —$CF_3$ in ortho and the other $R^1$ is —CN in meta position to the attachment position of the benzene moiety;

$F_l$ is —C(=O)—, with l being 1, q of $K_q$ is 0, $K_p$ is $C_1$-alkyl, n of $R^1{}_n$ is 1, $R^1$ is —$SCF_3$, —$SOCF_3$, —$SO_2CF_3$ in para position to the attachment position of the benzene moiety;

$F_l$ is —C(=O)—, with l being 1, q of $K_q$ is 0, $K_p$ is $C_1$-alkyl, n of $R^1{}_n$ is 1, $R^1$ is —$SCF_3$ in para position to the attachment position of the benzene moiety;

$F_l$ is —C(=O)—, with l being 1, q of $K_q$ is 0, $K_p$ is $C_2$-alkyl, n of $R^1{}_n$ is 1, $R^1$ is —$SCF_3$, —$SOCF_3$, —$SO_2CF_3$ in para position to the attachment position of the benzene moiety;

$F_l$ is —C(=O)—, with l being 1, q of $K_q$ is 0, $K_p$ is $C_2$-alkyl, n of $R^1{}_n$ is 1 and $R^1$ is —$SCF_3$ in para position to the attachment position of the benzene moiety;

l of $F_l$ is 0, q of $K_q$ is 0, p of $K_p$ is 0;

l of $F_l$ is 0, q of $K_q$ is 0, p of $K_p$ is 0, n of $R^1{}_n$ is 2;

l of $F_l$ is 0, q of $K_q$ is 0, p of $K_p$ is 0, n of $R^1{}_n$ is 2, one of the two $R^1$ is in ortho and the other $R^1$ is in meta position to the attachment position of the benzene moiety;

l of $F_l$ is 0, q of $K_q$ is 0, p of $K_p$ is 0, n of $R^1{}_n$ is 2, one of the two $R^1$ is —$CF_3$ in ortho and the other $R^1$ is —CN in meta position to the attachment position of the benzene moiety;

l of $F_l$ is 0, q of $K_q$ is 0, p of $K_p$ is 0, n of $R^1{}_n$ is 1;

l of $F_l$ is 0, q of $K_q$ is 0, p of $K_p$ is 0, n of $R^1{}_n$ is 1 and $R^1$ is in pare position to the attachment position of the benzene moiety;

l of $F_l$ is 0, q of $K_q$ is 0, p of $K_p$ is 0, n of $R^1{}_n$ is 1 and $R^1$ is —$SCF_3$, —$SOCF_3$, —$SO_2CF_3$ in para position to the attachment position of the benzene moiety;

l of $F_l$ is 0, q of $K_q$ is 0, p of $K_p$ is 0, n of $R^1{}_n$ is 1 and $R^1$ is —$SCF_3$ in para position to the attachment position of the benzene moiety;

l of $F_l$ is 0, q of $K_q$ is 0, $K_p$ is $C_1$- or $C_2$-alkyl;

l of $F_l$ is 0, p of $K_p$ is 0, $K_q$ is $C_1$- or $C_2$-alkyl;

l of $F_l$ is 0, p of $K_p$ is 0, $K_q$ is $C_1$- or $C_2$-alkyl, n of $R^1{}_n$ is 1 or 2;

$F_l$ is 0, q of $K_q$ is 0, $K_p$ is $C_1$- or $C_2$-alkyl, n of $R^1{}_n$ is 2;

$F_l$ is 0, q of $K_q$ is 0, $K_p$ is $C_1$- or $C_2$-alkyl, n of $R^1{}_n$ is 2, one of the two $R^1$ is in ortho and the other $R^1$ is in meta position to the attachment position of the benzene moiety;

$F_l$ is 0, q of $K_q$ is 0, $K_p$ is $C_1$- or $C_2$-alkyl, n of $R^1{}_n$ is 2, one of the two $R^1$ is —$CF_3$ in ortho and the other $R^1$ is —CN in meta position to the attachment position of the benzene moiety;

$F_l$ is 0, q of $K_q$ is 0, $K_p$ is $C_1$- or $C_2$-alkyl, n of $R^1{}_n$ is 1;

$F_l$ is 0, q of $K_q$ is 0, $K_p$ is $C_1$- or $C_2$-alkyl, n of $R^1{}_n$ is 1 and $R^1$ in para position to the attachment position of the benzene moiety;

$F_l$ is 0, q of $K_q$ is 0, $K_p$ is $C_1$- or $C_2$-alkyl, n of $R^1{}_n$ is 1 and $R^1$ is —$SCF_3$, —$SOCF_3$, —$SO_2CF_3$ in para position to the attachment position of the benzene moiety;

l of $F_l$ is 0, q of $K_q$ is 0, $K_p$ is $C_1$- or $C_2$-alkyl, n of $R^1{}_n$ is 1 and $R^1$ is —$SCF_3$ in para position to the attachment position of the benzene moiety;

wherein—if not stated otherwise—each of the above mentioned $R^1{}_n$ is selected independently from any possible other $R^1$, from the group —C(=O)O$R^2$, —C(=O)N$R^2{}_2$, —C(=O)S$R^2$, —C(=S)O$R^2$, —C(NH)N$R^2{}_2$, $CN_4H_2$, —N$R^2{}_2$, —C(=O)$R^2$, —C(=S)$R^2$, —O$R^2$, —S$R^2$, —$CF_3$, —$OCF_3$, —$SCF_3$, —$SOCF_3$, —$SO_2CF_3$, —CN, —$NO_2$, —F, —Cl, —Br or —I.

In some embodiments, OM is a metal sandwich complex of the general formula (2c),

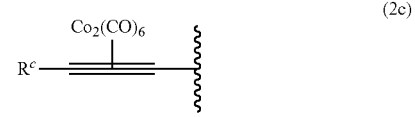

(2c)

wherein $R^c$ is selected from
  hydrogen,
  an unsubstituted or substituted $C_1$-$C_{10}$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy,
  an unsubstituted or substituted $C_6$-$C_{14}$ aryl,
  an unsubstituted or substituted 5- to 10-membered heteroaryl, wherein 1 to 4 ring atoms are independently selected from nitrogen, oxygen or sulfur,
  an unsubstituted or substituted 5- to 10-membered heteroalicyclic ring, wherein 1 to 3 ring atoms are independently nitrogen, oxygen or sulfur,
  —O$R^3$, —S$R^3$, —C(O)$R^3$, —C(S)$R^3$, —C(O)O$R^3$, —C(S)O$R^3$, —C(O)S$R^3$, —C(O)N$R^3R^4$, —N$R^3R^4$, —S(O)$_2R^3$, —S(O)$_2$O$R^3$, and —S(O)$_2$N$R^3R^4$,
  wherein
    $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, $R^c$ of the general formula 2c is selected from —O$R^3$, —S$R^3$, —C(O)$R^3$, —C(S)$R^3$, —C(O)O$R^3$, —C(S)O$R^3$, —C(O)S$R^3$, —C(O)N$R^3R^4$, —N$R^3R^4$, —S(O)$_2R^3$, —S(O)$_2$O$R^3$, and —S(O)$_2$N$R^3R^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

In some embodiments, $R^c$ of the general formula 2c is hydrogen.

In some embodiments, $R^c$ of the general formula 2c is an unsubstituted or substituted $C_1$-$C_{10}$ alkyl, an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy In some embodiments, $R^c$ of the general formula 2c is a group as defined above, and

- $F_l$ is —C(=O)— or —C(=S), with l being 1, q of $K_q$ is 0, p of $K_p$ is 0;
- $F_l$ is —C(=O)—, with l being 1, q of $K_q$ is 0, p of $K_p$ is 0;
- $F_l$ is —C(=O)— or —C(=S), with l being 1, q of $K_q$ is 0, $K_p$ is $C_1$- or $C_2$-alkyl;
- $F_l$ is —C(=O)—, with l being 1, q of $K_q$ is 0, $K_p$ is $C_1$- or $C_2$-alkyl;
- $F_l$ is —C(=O)—, with l being 1, p of $K_p$ is 0, $K_q$ is $C_1$- or $C_2$-alkyl;
- $F_l$ is —C(=O)—, with l being 1, p of $K_p$ is $C_1$- or $C_2$-alkyl, $K_q$ is $C_1$- or $C_2$-alkyl;
- $F_l$ is —C(=O)— with l being 1, q of $K_q$ is 0, p of $K_p$ is 0, n of $R^1_n$ is 2;
- $F_l$ is —C(=O)—, with l being 1, q of $K_q$ is 0, p of $K_p$ is 0, n of $R^1_n$ is 2, one of the two $R^1$ is in ortho and the other $R^1$ is in meta position to the attachment position of the benzene moiety
- $F_l$ is —C(=O)—, with l being 1, q of $K_q$ is 0, p of $K_p$ is 0, n of $R^1_n$ is 2, one of the two $R^1$ is —$CF_3$ in ortho and the other $R^1$ is —CN in meta position to the attachment position of the benzene moiety;
- $F_l$ is —C(=O)—, with l being 1, q of $K_q$ is 0, p of $K_p$ is 0, n of $R^1_n$ is 1;
- $F_l$ is —C(=O)—, with l being 1, q of $K_q$ is 0, p of $K_p$ is 0, n of $R^1_n$ is 1; $R^1$ is in para position to the attachment position of the benzene moiety;
- $F_l$ is —C(=O)—, with l being 1, q of $K_q$ is 0, p of $K_p$ is 0, n of $R^1_n$ is 1; $R^1$ is —$SCF_3$, —$SOCF_3$, —$SO_2CF_3$ in para position to the attachment position of the benzene moiety;
- $F_l$ is —C(=O)—, with l being 1, q of $K_q$ is 0, p of $K_p$ is 0, n of $R^1_n$ is 1 and $R^1$ is —$SCF_3$ in para position to the attachment position of the benzene moiety;
- $F_l$ is —C(=O)—, with l being 1, q of $K_q$ is 0, $K_p$ is $C_1$- or $C_2$-alkyl, n of $R^1_n$ is 2, one of the two $R^1$ is —$CF_3$ in ortho and the other $R^1$ is —CN in meta position to the attachment position of the benzene moiety;
- $F_l$ is —C(=O)—, with l being 1, q of $K_q$ is 0, $K_p$ is $C_1$-alkyl, n of $R^1_n$ is 1, $R^1$ is —$SCF_3$, —$SOCF_3$, —$SO_2CF_3$ in para position to the attachment position of the benzene moiety;
- $F_l$ is —C(=O)—, with l being 1, q of $K_q$ is 0, $K_p$ is $C_1$-alkyl, n of $R^1_n$ is 1, $R^1$ is —$SCF_3$ in para position to the attachment position of the benzene moiety;
- F is —C(=O)—, with l being 1, q of $K_q$ is 0, $K_p$ is $C_2$-alkyl, n of $R^1_n$ is 1, $R^1$ is —$SCF_3$, —$SOCF_3$, —$SO_2CF_3$ in para position to the attachment position of the benzene moiety;
- $F_l$ is —C(=O)—, with l being 1, q of $K_q$ is 0, $K_p$ is $C_2$-alkyl, n of $R^1_n$ is 1 and $R^1$ is —$SCF_3$ in para position to the attachment position of the benzene moiety;
- l of $F_l$ is 0, q of $K_q$ is 0, p of $K_p$ is 0;
- l of $F_l$ is 0, q of $K_q$ is 0, p of $K_p$ is 0, n of $R^1_n$ is 2;
- l of $F_l$ is 0, q of $K_q$ is 0, p of $K_p$ is 0, n of $R^1_n$ is 2, one of the two $R^1$ is in ortho and the other $R^1$ is in meta position to the attachment position of the benzene moiety;
- l of $F_l$ is 0, q of $K_q$ is 0, p of $K_p$ is 0, n of $R^1_n$ is 2, one of the two $R^1$ is —$CF_3$ in ortho and the other $R^1$ is —CN in meta position to the attachment position of the benzene moiety;
- l of $F_l$ is 0, q of $K_q$ is 0, p of $K_p$ is 0, n of $R^1_n$ is 1;
- l of $F_l$ is 0, q of $K_q$ is 0, p of $K_p$ is 0, n of $R^1_n$ is 1 and $R^1$ is in para position to the attachment position of the benzene moiety;
- l of $F_l$ is 0, q of $K_q$ is 0, p of $K_p$ is 0, n of $R^1_n$ is 1 and $R^1$ is —$SCF_3$, —$SOCF_3$, —$SO_2CF_3$ in para position to the attachment position of the benzene moiety;
- l of $F_l$ is 0, q of $K_q$ is 0, p of $K_p$ is 0, n of $R^1_n$ is 1 and $R^1$ is —$SCF_3$ in para position to the attachment position of the benzene moiety;
- l of $F_l$ is 0, q of $K_q$ is 0, $K_q$ is $C_1$- or $C_2$-alkyl;
- l of $F_l$ is 0, p of $K_p$ is 0, $K_q$ is $C_1$- or $C_2$-alkyl;
- l of $F_l$ is 0, p of $K_p$ is 0, $K_q$ is $C_1$- or $C_2$-alkyl, n of $R^1_n$ is 1 or 2;
- $F_l$ is 0, q of $K_q$ is 0, $K_q$ is $C_1$- or $C_2$-alkyl, n of $R^1_n$ is 2;
- $F_l$ is 0, q of $K_q$ is 0, $K_p$ is $C_1$- or $C_2$-alkyl, n of $R^1_n$ is 2, one of the two $R^1$ is in ortho and the other $R^1$ is in meta position to the attachment position of the benzene moiety;
- $F_l$ is 0, q of $K_q$ is 0, $K_p$ is $C_1$- or $C_2$-alkyl, n of $R^1_n$ is 2, one of the two $R^1$ is —$CF_3$ in ortho and the other $R^1$ is —CN in meta position to the attachment position of the benzene moiety;
- $F_l$ is 0, q of $K_q$ is 0, $K_p$ is $C_1$- or $C_2$-alkyl, n of $R^1_n$ is 1;
- $F_l$ is 0, q of $K_q$ is 0, $K_q$ is $C_1$- or $C_2$-alkyl, n of $R^1_n$ is 1 and $R^1$ in para position to the attachment position of the benzene moiety;
- $F_l$ is 0, q of $K_q$ is 0, $K_p$ is $C_1$- or $C_2$-alkyl, n of $R^1_n$ is 1 and $R^1$ is —$SCF_3$, —$SOCF_3$, —$SO_2CF_3$ in para position to the attachment position of the benzene moiety;
- l of $F_l$ is 0, q of $K_q$ is 0, $K_p$ is $C_r$ or $C_2$-alkyl, n of $R^1_n$ is 1 and $R^1$ is —$SCF_3$ in para position to the attachment position of the benzene moiety;

wherein—if not stated otherwise—each of the above mentioned $R^1_n$ is selected independently from any possible other $R^1_n$ from the group —C(=O)$OR^2$, —C(=O)$NR^2_2$, —C(=O)$SR^2$, —C(=S)$OR^2$, —C(NH)$NR^2_2$, $CN_4H_2$, —$NR^2_2$, —C(=O)$R^2$, —C(=S)$R^2$, —$OR^2$, —$SR^2$, —$CF_3$, —$OCF_3$, —$SCF_3$, —$SOCF_3$, —$SO_2CF_3$, —CN, —$NO_2$, —F, —Cl, —Br or —I.

Particular embodiments of this aspect of the invention are:

a. N-(1-(ferrocenyloxy)-2-cyanopropan-2-yl)-4-((trifluoromethyl)thio)benzamide

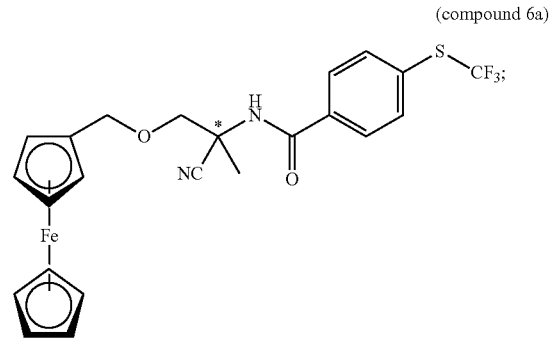

(compound 6a)

b. 2-cyano-2-(4-((trifluoromethyl)thio)benzamido)propyl ferrocenoate (compound 8a)

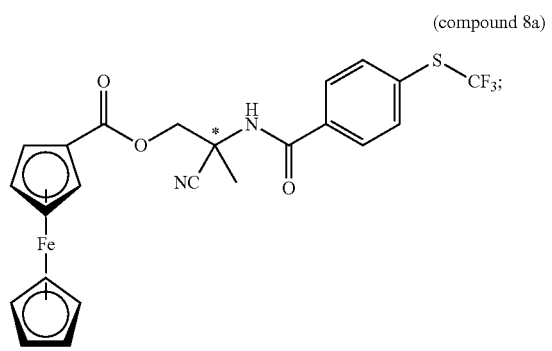

c. 2-cyano-2-(4-((trifluoromethyl)sulfinyl)benzamido) propyl ferrocenoate (compound 8b)

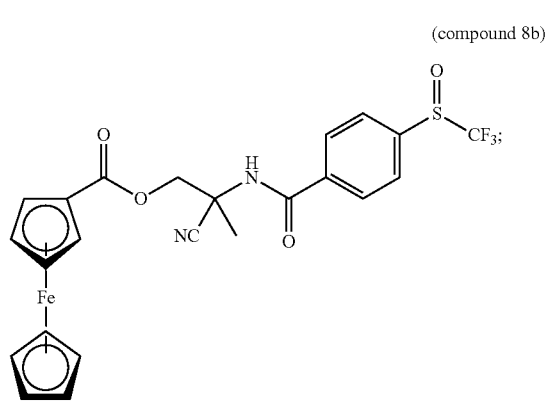

d. 2-cyano-2-(4-((trifluoromethyl)sulfonyl)benzamido) propyl ferrocenoate (compound 8c)

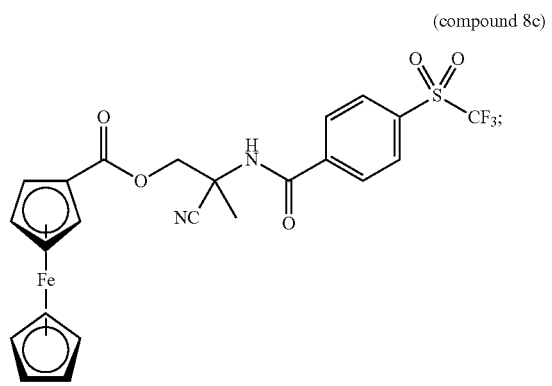

e. 2-cyano-2-(4-((trifluoromethoxy)benzamido)propyl ferrocenoate (compound 8d)

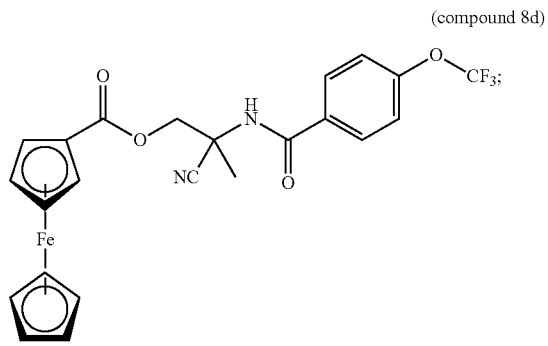

f. 2-cyano-2-(4-(trifluoromethyl)benzamido)propyl ferrocenoate (compound 8e)

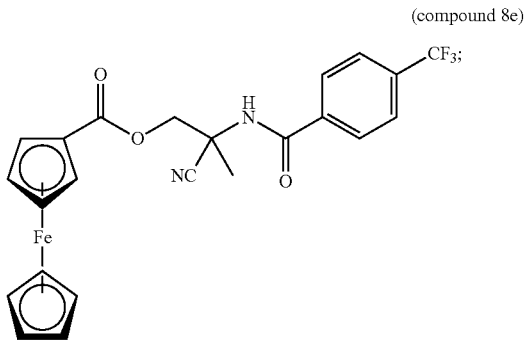

g. 2-cyano-2-2(4-(methylthio)benzamido)propyl ferrocenoate (compound 8f)

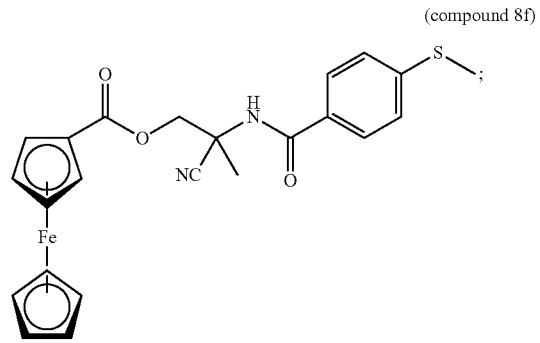

h. 2-cyano-2-(4-fluorobenzamido)propyl ferrocenoate (compound 8g)

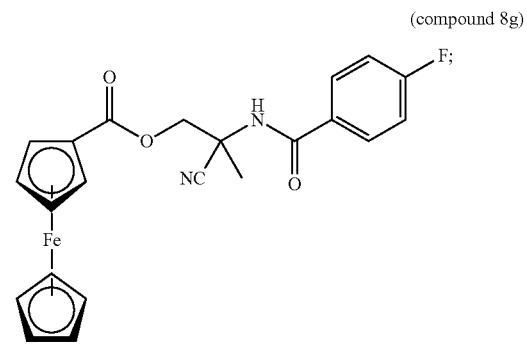

i. 2-(4-chlorobenzamido)-2-cyanopropyl ferrocenoate (compound 8h)

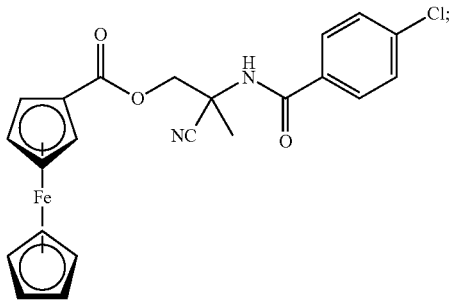

j. 2-(4-bromobenzamido)-2-cyanopropyl ferrocenoate (compound 8i)

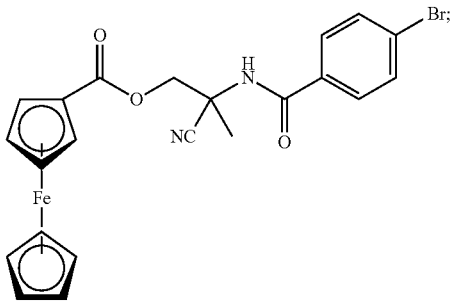

k. 2-cyano-2-(4-iodobenzamido)propyl ferrocenoate (compound 8j)

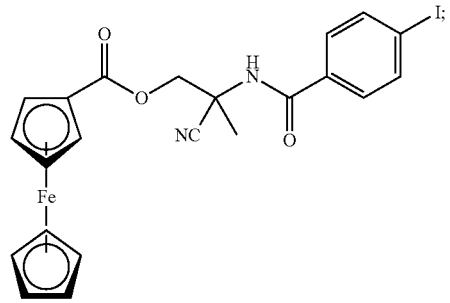

l. 2-cyano-2-(4-((trifluoromethyl)thio)benzamido)propyl ruthenocenoate (compound 8k)

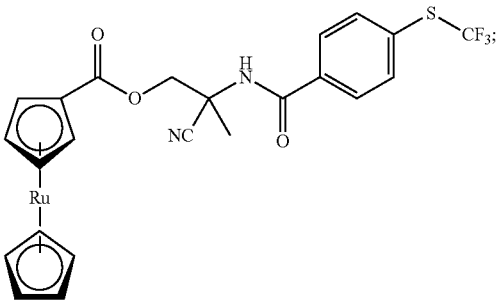

m. Co2(CO)6 complex of 2-cyano-2-(4-((trifluoromethyl)thio)benzamido)propyl propiolate (compound 10a)

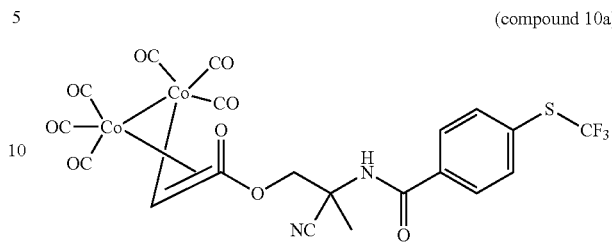

n. 2-cyano-2-(4-((trifluoromethyl)thio)benzamido)propyl cymantrenoate (compound 11a)

The compounds of the general formula (1) can also be obtained in the form of their hydrates and/or also can include other solvents used for example for the crystallization of compounds present in the solid form. Depending on the method and/or the reaction conditions, compounds of the general formula (1) can be obtained in the free form or in the form of salts.

The compounds of the general formula (1) may be present as optical isomers or as mixtures thereof. The stereocenter is marked with an asterisk in the formulas and is located on the C1 carbon atom of the ethyl moiety. The invention relates both to the pure isomers, racemic mixtures and all possible isomeric mixtures and is hereinafter understood as doing so, even if stereochemical details are not specifically mentioned in every case. Diastereoisomeric mixtures of compounds of the general formula (1), which are obtainable by the process or any other way, may be separated in known manner—on the basis of the physical-chemical differences of their components—into pure diastereoisomers, for example by fractional crystallisation, distillation and/or chromatography, in particular by preparative HPLC using a chiral HPLC column.

If not stated otherwise a racemic mixture is used.

According to the invention, apart from separation of corresponding isomer mixtures, generally known methods of diastereoselective or enantioselective synthesis can also be applied to obtain pure diastereoisomers or enantiomers, e.g. by carrying out the method described hereinafter and using educts with correspondingly suitable stereochemistry.

It is advantageous to isolate or synthesise the biologically more active isomer, provided that the individual compounds have different biological activities.

A further object of the invention is the process for the preparation of the compounds described by the general formula (1).

The preparation comprises a compound described by the general formula (4)

(4)

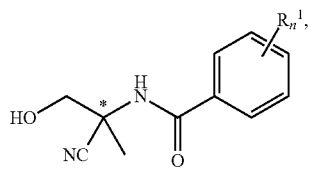

which is synthesised by an adapted synthesis according to Gauvry et al. (WO2005/044784 A1). The reaction pathway is depicted in scheme 1.

Scheme 1: The 2-amino-2-hydroxymethylpropionitrile 3a was produced according to Gauvry et al. (WO2005/044784 A1). $R_n^1$ of compound 3b has the meaning as defined above and Q of compound 3b is a leaving group, for example a leaving group as described in WO2005/044784 A1. Compounds 3a and 3b are known compounds, commercially available or may be produced analogously to known compounds. Compound 3a was reacted with one equivalent of 3b according to an adapted procedure of Gauvry et al. (WO2005/044784 A1), yielding compound 4.

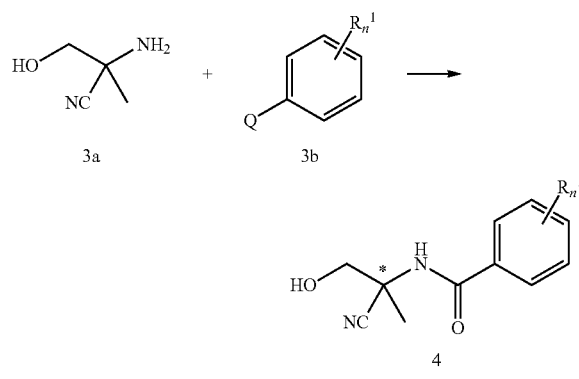

In one embodiment, compound 4 was treated with compound 5, according to an adapted procedure of Gasser et al. (G. Gasser, A. J. Fischmann, C. M. Forsyth and L. Spiccia, *J. Organomet. Chem.*, 2007, 692, 3835-3840), yielding compound 6. The reaction pathway is depicted in scheme 2.

Scheme 2: Compound 4 was reacted with compound 5, according to an adapted procedure of Gasser et al. (*J. Organomet. Chem.* 2007, 692, 3835-3840) was Gasser et al. (*J. Med. Chem.* 2012, 55, 8790-8798). $R_n^1$, $R_y^L$, $R_z^U$, Y and p of $K_p$ have the same meaning as defined above. Compound 5 (see scheme 3) is formed by a reaction of the organometallic moity OM of the formula 2a according to a synthetic method similar to the method employed by Gasser et al. (*J. Organomet. Chem.* 2007, 692, 3835-3840).

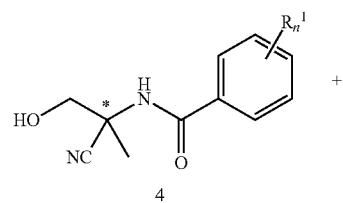

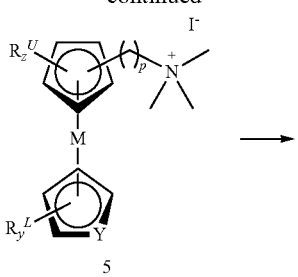

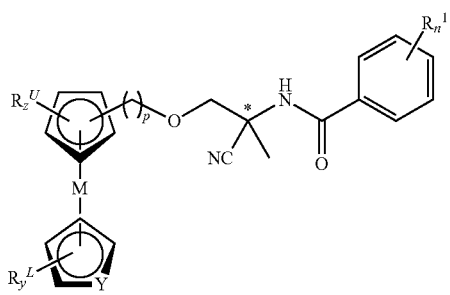

Scheme 3: Formation of compound 5 from compound 5' according to a synthetic method similar to the method employed by Gasser et al. (*J. Organomet. Chem.* 2007, 692, 3835-3840). Compound 5' comprising the substituents $R_y^L$, $R_z^U$, Y as defined above, is a known compound, which can be purchased or may be synthesized by known procedures or may be prepared analogously to known compounds. Such procedures are described by, without being limited to it, Patra et al. (*J. Med. Chem.* 2012, 55, 8790-8798; Apreutesei et al. (*Appl. Organomet. Chem.* 2005, 19, 1022-1037), Bonini et al. (*Eur. J. Org. Chem.* 2002, 543-550); Routaboul et al. (*J. Organomet. Chem.* 2001, 637, 364-371).

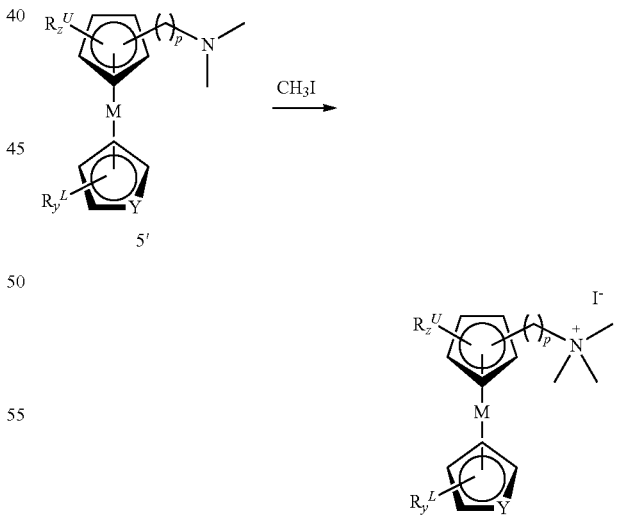

In one embodiment, compound 4 was reacted with compound 7, according to an adapted procedure of Gasser et al. (*J. Med. Chem.* 2012, 55, 8790-8798), yielding compound 8. The reaction pathway is depicted in scheme 4.

Scheme 4:
Compound 4 was reacted with compound 7, according to an adapted procedure of Gasser et. al. (*J. Med. Chem.* 2012, 2012, 55, 8790-8798). $R_n^1$, $R_y^L$, $R_z^U$, Y and p of $K_p$ have the meaning as defined above. W is O or S and Q is a leaving group. In some embodiments, W is O and Q is Cl and the reaction takes place in the presence of $NEt_3$ In some embodiments, W is O and Q is OH and the reaction takes place in the presence of HATU (O-(7-azabenzotriazol-1-yl)-N,N,N',N'-tetramethyluronium-hexafluorophosphate), DIPEA (N,N-Diisopropylethylamine) in N,N-dimethylformamid (comparable to the procedure of Patra et al. (*Organometallics*, 2010, 29, 4312-4319)). Optionally, an alkyl group $K_q$ (with the meaning as defined above) may be introduced between then —C=W moiety (with W being O or S) and the leaving group Q. The organometallic moiety OM of compound 7 (comparable to the general formula 2a) is the same as the organometallic moiety of compound 5 and 5', as described above. Reference is made to the above cited conditions, references and reaction pathways. Compound 7, which comprises the substituents $R_y^L$, $R_z^U$, Y as defined above, is a known compound, which can be purchased or may be synthesized by known procedures or may be prepared analogously to known compounds starting from the organometallic moiety OM of compound 7, as defined above (see for example Patra, M.; Ingram, K.; Pierroz, V.; Ferrari, S.; Spingler, B.; Keiser, J.; Gasser, G., *J. Med. Chem.* 2012, 55, 8790-8798 and reference therein).

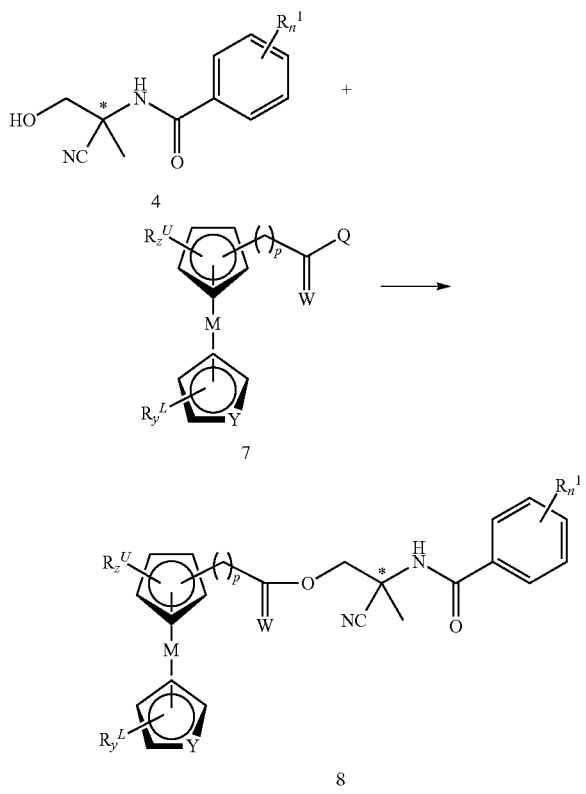

Reaction pathways for compounds comprising the half metal sandwich complexes OM of the general formula 2b follow a similar pathway as the above mentioned reactions, in particular a similar pathway as depicted in scheme 2 and scheme 4, which are easily adaptable for a person skilled in the art. Reference is made to the above cited conditions, references and reactions pathways.

A reaction pathway for compounds comprising carbonyl complexes OM of the general formula 2c is depicted in scheme 5.

Scheme 5: Compound 4 was reacted with compound 9 in the presence of NaH in THF, yielding compound 10. X is a group described by a general formula —$K_p$—$F_i$—$K_q$—. Furthermore, $R_n^1$, $R_y^L$, $R_z^U$, Y, p, $K_p$, I, $F_i$, q, $K_q$ have the same meaning as defined above. Compound 9 is a known compound, which can be purchased or may be synthesized by known procedures or may be prepared analogously to known compounds. Compound 10 is then reacted with $Co_2(CO)_8$ according to a synthetic method employed by Gasser et al. (*Inorg. Chem.* 2009, 48, 3157-3166), yielding compound 11.

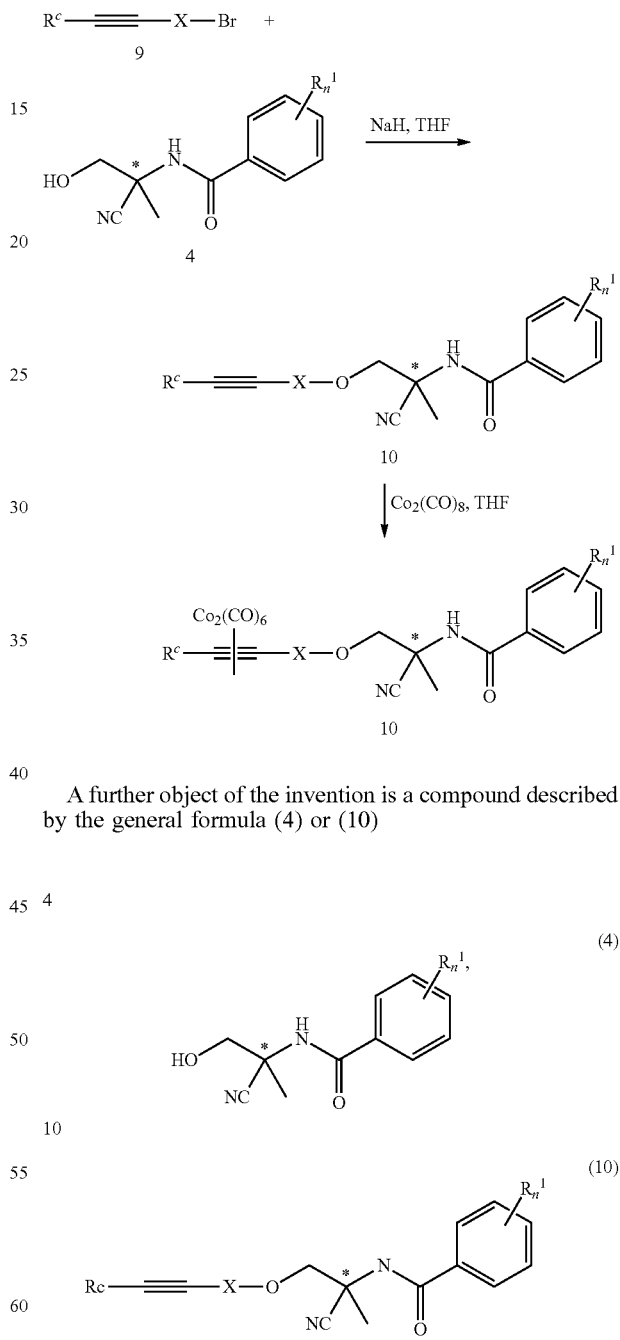

A further object of the invention is a compound described by the general formula (4) or (10)

with X, $R_n^1$ and $R_c$ having the same meaning as defined in the first aspect of the invention.

According to a third aspect of the invention, the compounds defined as the first aspect of the invention are provided for use in a method for treatment of disease.

A further aspect of the invention relates to the compounds described by the general formula (4) or (10) for use in a method for treatment of disease, in particular for use in a method for treatment of infections by helminths, or for use in a method to suppress plant helminths.

Pharmaceutically acceptable salts of the compounds provided herein are deemed to be encompassed by the scope of the present invention.

According to one aspect of the invention, a pharmaceutical composition for preventing or treating helminth infection, particularly infection by tapeworms (cestodes), flukes (trematodes) and roundworms (nematodes), in particular species of *Haemonchus, Trichstrongylus, Teladorsagia, Cooperia, Oesophagostomum* and/or *Chabertia*, tapeworm infection, schistosomiasis, ascariasis, dracunculiasis, elephantiasis, enterobiasis, filariasis, hookworm infection, onchocerciasis, trichinosis and/or trichuriasis is provided, comprising a compound according to the above aspect or embodiments of the invention.

Pharmaceutical compositions for enteral administration, such as nasal, buccal, rectal or, especially, oral administration, and for parenteral administration, such as dermal (spot-on), intradermal, subcutaneous, intravenous, intrahepatic or intramuscular administration, may be used. The pharmaceutical compositions comprise approximately 1% to approximately 95% active ingredient, preferably from approximately 20% to approximately 90% active ingredient.

According to one aspect of the invention, a dosage form for preventing or treating helminth infection, particularly infection by particularly tapeworms (cestodes), flukes (trematodes) and roundworms (nematodes), tapeworm infection, schistosomiasis, ascariasis, dracunculiasis, elephantiasis, enterobiasis, filariasis, hookworm infection, onchocerciasis, trichinosis and/or trichuriasis is provided, comprising a compound according to the above aspect or embodiments of the invention. Dosage forms may be for administration via various routes, including nasal, buccal, rectal, transdermal or oral administration, or as an inhalation formulation or suppository. Alternatively, dosage forms may be for parenteral administration, such as intravenous, intrahepatic, or especially subcutaneous, or intramuscular injection forms. Optionally, a pharmaceutically acceptable carrier and/or excipient may be present.

According to one aspect of the invention, a method for manufacture of a medicament for preventing or treating helminth infection, particularly infection by particularly tapeworms (cestodes), flukes (trematodes) and roundworms (nematodes), tapeworm infection, schistosomiasis, ascariasis, dracunculiasis, elephantiasis, enterobiasis, filariasis, hookworm infection, onchocerciasis, trichinosis and/or trichuriasisis provided, comprising the use of a compound according to the above aspect or embodiments of the invention. Medicaments according to the invention are manufactured by methods known in the art, especially by conventional mixing, coating, granulating, dissolving or lyophilizing.

According to one aspect of the invention, a method for preventing or treating helminth infection, particularly the indications mentioned previously, is provided, comprising the administration of a compound according to the above aspects or embodiments of the invention to a patient in need thereof.

The treatment may be for prophylactic or therapeutic purposes. For administration, a compound according to the above aspect of the invention is preferably provided in the form of a pharmaceutical preparation comprising the compound in chemically pure form and optionally a pharmaceutically acceptable carrier and optionally adjuvants. The compound is used in an amount effective against helminth infection. The dosage of the compound depends upon the species, the patient age, weight, and individual condition, the individual pharmacokinetic data, mode of administration, and whether the administration is for prophylactic or therapeutic purposes. The daily dose administered ranges from approximately 1 µg/kg to approximately 1000 mg/kg, preferably from approximately 1 µg to approximately 100 µg, of the active agent according to the invention.

Wherever reference is made herein to an embodiment of the invention, and such embodiment only refers to one feature of the invention, it is intended that such embodiment may be combined with any other embodiment referring to a different feature. For example, every embodiment that defines OM may be combined with every embodiment that defines $R^1$, $F_I$ or $K_p$, to characterize a group of compounds of the invention or a single compound of the invention with different properties.

The invention is further characterized, without limitations, by the following examples and figure, from with further features, advantages or embodiments can be derived. The examples and figures do not limit but illustrate the invention.

SHORT DESCRIPTION OF THE FIGURES

Figure 2:
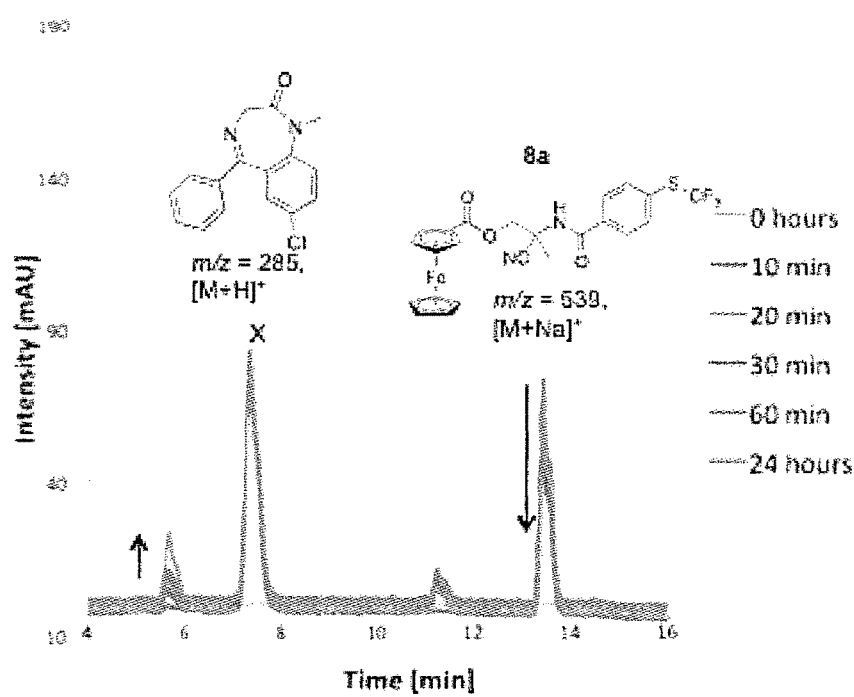
Figure 3:
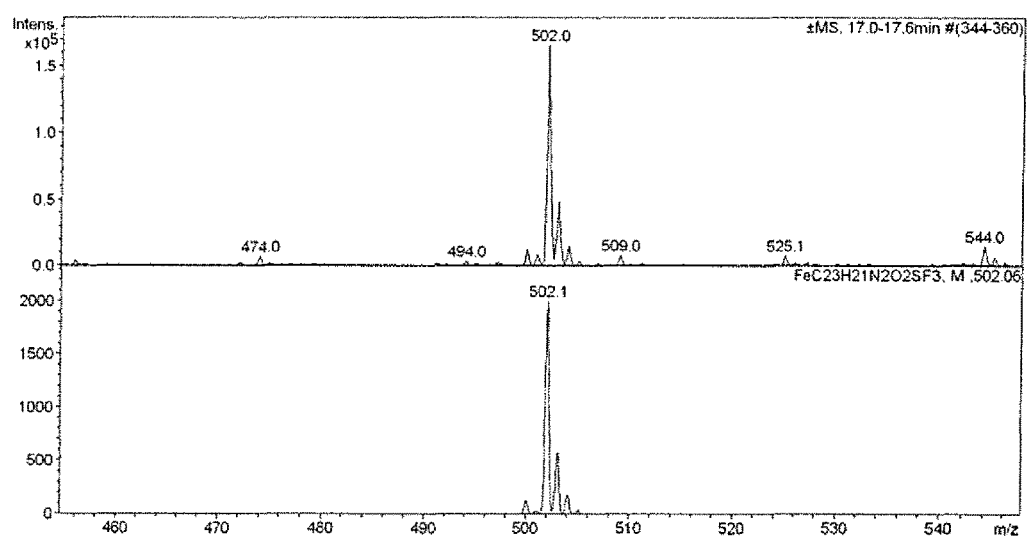

FIG. 1 shows the effect of compound 8a on a *C. elegans* worm suspension. The number of dead or immobile worms after an incubation of 24 h is displayed;

FIG. 2 shows the behaviour of compound 8a under physiological conditions, whereby the stability was assessed in sheep plasma. Compound 8a and diazepam (internal standard) were incubated at 37° C. for different time intervals and their stability was checked using an LC-MS technique. The peak at 13.41 min, which is corresponding to 8a, is decreasing within 24 hours while a new peak is arising at 5.64 min, which is corresponding to the hydrolysed product of 8a;

FIG. 3: shows an isotopic distribution pattern of integrated peaks at a retention time of 17.4 min (a) and a simulated isotopic distribution pattern of compound 6a (b).

GENERAL METHODS

Materials:

All chemicals were of reagent grade quality or better, obtained from commercial suppliers and used without further purification. Solvents were used as received or dried over 4 Å and 3 Å molecular sieves. THF and $Et_2O$ were freshly distilled under $N_2$ by employing standard procedures.[57] All syntheses were carried out using standard Schlenk techniques.

Instrumentation and Methods:

$^1$H- and $^{13}$C-NMR spectra were recorded in deuterated solvents on a Bruker DRX 400 or AV2 500 at 30° C. The chemical shifts δ, are reported in ppm. The residual solvent peaks have been used as internal reference. The abbreviations for the peak multiplicities are as follows: s (singlet), d (doublet), dd (doublet of doublet), t (triplet), q (quartet), m (multiplet) and br (broad). Infrared spectra were recorded on a PerkinElmer spectrum BX TF-IR spectrometer and KBr presslings were used for solids. Signal intensities are abbreviated w (weak), m (medium), s (strong) and br (broad). ESI mass spectra were recorded on a Bruker Esquire 6000 or on a Bruker maxis QTOF-MS instrument (Bruker Daltonics GmbH, Bremen, Germany). The LC-MS spectra were measured on an Acquity™ from Waters system equipped with a PDA detector and an auto sampler using an Agilent Zorbax 300SB-C18 analytical column (5.0 μm particle size, 100 Å pore size, 150×3.0 mm) or an Macherey—Nagel 100—5 C18 (3.5 μm particle size, 300 Å pore size, 150×3.0 mm). This LC was coupled to an Esquire HCT from Bruker (Bremen, Germany) for the MS measurements. The LC run (flow rate: 0.3 mL min-1) was performed with a linear gradient of A (distilled water containing 0.1% v/v formic acid) and B (acetonitrile (Sigma-Aldrich HPLC-grade), t=0 min, 5% B; t=3 min, 5% B; t=17 min, 100% B; t=20 min, 100% B; t=25 min, 5% B. High-resolution ESI mass spectra were recorded on a Bruker maxis QTOF-MS instrument (Bruker Daltonics GmbH, Bremen, Germany). The samples (around 0.5 mg) were dissolved in 0.5 mL of $MeCN/H_2O$ 1:1+0.1% HCOOH. The solution was then diluted 10:1 and analysed via continuous flow injection at 3 $\mu l \cdot min^{-1}$. The mass spectrometer was operated in the positive electrospray ionization mode at 4000 V capillary voltage, −500 V endplate offset, with a $N_2$ nebulizer pressure of 0.4 bar and dry gas flow of 4.0 l/min at 180° C. MS acquisitions were performed in the full scan mode in the mass range from m/z 100 to 2000 at 20,000 resolution and 1 scan per second. Masses were calibrated with a 2 mmol/l solution of sodium formate over m/z 158 to 1450 mass range with an accuracy below 2 ppm.

Cell Culture:

Human cervical carcinoma cells (HeLa) were cultured in DMEM (Gibco) supplemented with 5% fetal calf serum (FCS, Gibco), 100 U/ml penicillin, 100 μg/ml streptomycin at 37° C. and 5% $CO_2$. The normal human fetal lung fibroblast MRC-5 cell line was maintained in F-10 medium (Gibco) supplemented with 10% FCS (Gibco), 200 mmol/l L-Glutamine, 100 U/ml penicillin, and 100 μg/ml streptomycin at 37° C. and 5% CO2. To establish the anticancer potential of the compounds they were tested in one cell line, namely HeLa by a fluorometric cell viability assay using Resazurin (Promocell GmbH). Compounds showing cytotoxicity were then tested on normal MRC-5 cells. 1 day before treatment, cells were plated in triplicates in 96-well plates at a density of $4 \times 10^3$ cells/well in 100 μl for HeLa and $7 \times 10^3$ cells/well for MRC-5 cells. Cells were treated with increasing concentrations of the compounds for 2 days. After 2 days, medium and drug were removed and 100 ml fresh medium containing Resazurin (0.2 mg/ml final concentration) were added. After 4 h of incubation at 37° C., the highly red fluorescent dye resorufin's fluorescence was quantified at 590 nm emission with 540 nm excitation wavelength in the SpectraMax M5 microplate Reader.

C. elegans Movement Inhibition Assay:

Asynchronous N2 C. elegans worms (Bristol) were maintained on nematode growth medium (NGM) agar, seeded with a lawn on OP50 E coli as a food-source, according to standard protocol (*Maintenance of C. elegans*; Stiernagle, T., Ed.; WormBook, 2006.). Worms were harvested from NGM plates by washing with M9 buffer (42 mmol/l $Na_2HPO_4$, 22 mmol/l $KH_2PO_4$, 86 mmol/l NaCl and 1 mmol/l $MgSO_4$), aspiration and collection in a 10 mL tube (Falcon). The average number of worms in 5 μL of this suspension was calculated by transferring 4×5 μL aliquots to a glass slide (Menzel Glaser), and worms were enumerated under a compound microscope (Olympus CH30). To adjust the suspension to contain 1 worm per μL, M9 buffer was either added or removed after pelleting worms at 600×g for 30 sec.

Dilution of Test Compounds, Zolvix (Monepantel) and DMSO for Working Stock Solutions and 96 Well Plate Set-Up for Liquid Screen:

A volume of 70 μL of M9 buffer was added to each well in a 96-well plate, using a multichannel pipettor. A volume of 20 μL of worm suspension was added to each well using a single-channel pipettor, with a trimmed pipette tip (increased aperture to minimize damage to worms). The worm suspension was resuspended by flicking after every three wells to maintain consistency. GG compounds were stored at 4° C., and diluted in dimethyl sulfoxide (DMSO) to achieve a 100 mmol/l concentration 1 hr prior to addition to assay. These stock solutions were diluted further in DMSO to create a series of 20 mmol/l, 2 mmol/l, 0.02 mmol/l and 0.002 mmol/l which were subsequently diluted 1:20 in M9 buffer to create 1 mmol/l, 0.1 mmol/l, 1 μmol/l and 0.1 μmol/l (all 5% (v/v) DMSO). 10 μL of each concentration was added to wells in duplicate to achieve final concentrations of 100 μmol/l, 10 μmol/l, 100 nmol/l and 10 nmol/l in 100 μL (0.5% DMSO). A Zolvix (monepantel) dilution series was simultaneously created following the same dilution schema, and used as a positive control; 10 μL of 10% DMSO was added to achieve 1% DMSO vehicle control. 10 μL M9 was added to negative control wells (see FIG. 1). Plates were incubated at room temperature (22-24° C.) overnight at 20° C.

Quantitative Worm Mobility Scoring:

Immobile worms were counted as a percentage of total worms in each well using an Olympus SZ30 dissecting microscope. The immobile fraction was subtracted from the total, and this remainder was divided by the total to give a percentage of live worms per well. Descriptive and inferential statistics were deferred until further replicates are performed.

X-Ray Crystallography:

Crystallographic data for all compounds were collected at 183(2) K with Mo Kα radiation (λ=0.7107 Å) that was graphite-monochromated on a Stoe IPDS diffractometer. Suitable crystals were covered with oil (Infineum V8512, formerly known as Paratone N), mounted on top of a glass fibre or a CryoLoop™ (Hampton Research) and immediately transferred to the diffractometer. In the case of the IPDS, a maximum of eight thousand reflections distributed over the whole limiting sphere were selected by the program SELECT and used for unit cell parameter refinement with the program CELL (STOE & Cie, GmbH: Darmstadt, Germany, 199). Data were corrected for Lorentz and polarisation effects as well as for absorption (numerical). Structures were solved with direct methods using SIR97 (Altomare, A.; Burla, M. C.; Camalli, M.; Cascarano, G. L.; Giacovazzo, C.; Guagliardi, A.; Moliterni, A. G. G.; Polidori, G.; Spagna, R. *J. Appl. Cryst.* 1999, 32, 115-119) and were refined by full-matrix least-squares methods on F2 with SHELXL-97 (Sheldrick, G. M. *Acta Cryst.* 2008, A64, 112-122). The hydrogen atoms of the $NH_2$ units were localized and their positions freely refined. All other hydrogen atoms were placed on calculated positions. The structures were checked for higher symmetry with help of the program Platon (Spek, A. L. *J. Appl. Cryst.* 2003, 36, 7-139.

In vitro experiments can be conducted by testing compounds in a larval development assay. To do this, sheep are infected with infective third-stage larvae (L3) of species of *Haemonchus, Trichstrongylus, Teladorsagia, Cooperia, Oesophagostomum* or *Chabertia*. Faeces from these sheep are collected and used for experiments; ~100 g of faeces are crushed homogenized and suspended in ~1000 ml of sugar solution (specific gravity 1.2), put through a 'tea strainer' sieve, and the large undigested food material in the sieve discarded. The sugar solution is then placed into a flat dish and strips of plastic overhead transparency film placed on the surface. The plastic is left for at least 45 minutes to allow the eggs to stick and then removed carefully. The eggs are collected by washing them from the plastic film, with water, into a 50 ml centrifuge tube. The water containing egg suspension eggs is put through a 40 mm sieve to remove further plant material and then centrifuged at 1,000×g for 10 minutes. The supernatant is checked for eggs and then discarded as the majority of eggs are at the bottom of the tube. These eggs are collected in 1 ml of water and diluted to ~200 eggs/20 ml.

1. Each compound is tested at five concentrations: 100, 50, 25, 12.5 and 6.25 mmol/l (i.e. serial 2-fold dilutions starting from 100 mmol/l). Dilutions of each compound (10 ml in total) are performed in 1.5 ml microcentrifuge tubes, 1 ml of molten agar added, the tube vortexed and the agar aliquoted (150 ml) into the wells of a 96-well microtitre plate.
2. DMSO is used in a number of wells as solvent-only controls (negative controls) whilst cydectinis used as a positive control. Concentrations of cydectin used for positive controls for the compound re-testing are: 6.25, 12.5, 25, 50 and 100 mmol/l.
3. ~100 eggs (20 ml) are then added to each well.
4. Plates are then incubated overnight at 27° C.
5. Plates are checked the following morning and afternoon to ensure that most eggs had hatched. Any compounds that appeared to have an ovicidal effect are noted.
6. Following hatching of most eggs, 15 ml of nutritive medium is added to feed the larvae. Nutritive medium is prepared as follows: 1 g of yeast extract is added to 90 ml of 0.85% physiological saline and autoclaved for 20 mins at 121° C. Three milliliters of 10× Earle's balanced salt solution is added to 27 ml of yeast extract solution and the pH of the solution adjusted to 5.4-5.6 by the addition of bicarbonate.
7, Following 7 days additional incubation, the numbers of L3 larvae that had developed in each well is determined.

In vivo experiments can be conducted in sheep monospecifically infected with these parasites (i.e. species of *Haemonchus, Trichstrongylus, Teladorsagia, Cooperia, Oesophagostomum* or *Chabertia*)

Endo Parasites
Activity In Vitro Against *Dirofilaria immitis* (Di) (Filarial Nematodes).

Freshly harvested and cleaned microfilariae from blood from donor animals (dogs for Di).

The microfilariae are then distributed in formatted microplates containing the test substances to be evaluated for antiparasitic activity. Each compound is tested by serial dilution in order to determine its minimum effective dose (MED). The plates are incubated for 48 hours at 26° C. and 60% relative humidity (RH). Motility of microfilariae is then recorded to identify possible nematocidal activity.

Efficacy is expressed in percent reduced motility as compared to the control and standards.
Activity In Vitro Against *Haemonchus contortus* & *Trichostrongylus colubriformis* (Gastro-Intestinal Nematodes).

Freshly harvested and cleaned nematode eggs are used to seed a suitably formatted microplate containing the test substances to be evaluated for antiparasitic activity. Each compound is tested by serial dilution in order to determine its MED. The test compounds are diluted in nutritive medium allowing the full development of eggs through to 3rd instar larvae. The plates are incubated for 6 days at 28° C. and 60% relative humidity (RH). Egg-hatching and ensuing larval development are recorded to identify a possible nematocidal activity.

Efficacy is expressed in percent reduced egg hatch, reduced development of L3, or paralysis & death of larvae of all stages.

EXAMPLES OF SYNTHETIC PATHWAYS

Example 1: Synthesis of N-(1-(ferrocenyloxy)-2-cyanopropan-2-yl)-4-((trifluoromethyl)thio) benzamide (compound 6a)

The proposed synthetic pathway is depicted in Scheme 6.

Scheme 6: Acetonitrile, (ferrocenylmethyl)trimethylammonium iodide, $K_2CO_3$, 18-crown-6, reflux, overnight.

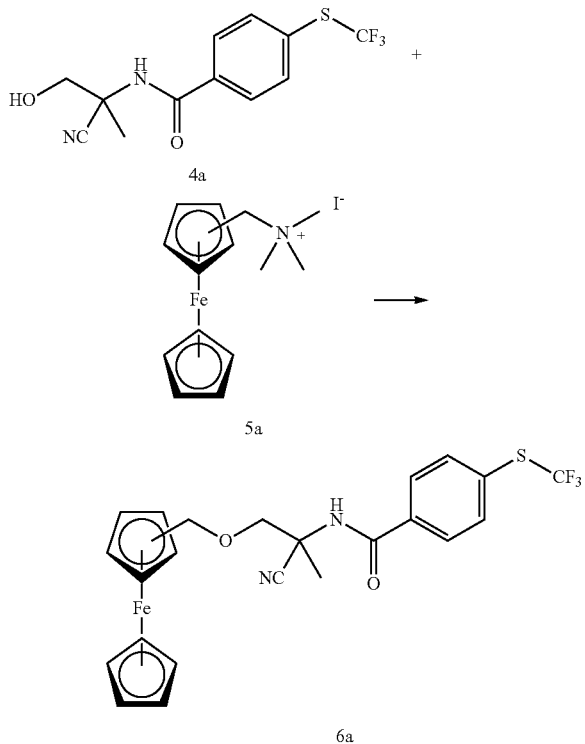

The 2-amino-2-hydroxymethylproprionitrile 3a, produced according to Gauvry et al. (WO2005/044784 A1), was treated with one equivalent of 4-(trifluoromethylthio)benzoyl chloride in the presence of triethylamine to obtain N-(2-cyano-1-hydroxypropan-2-yl)-4-((trifluoromethyl) thio)benzamide 4a in 32% yield. Subsequently 4a was treated with (ferrocenylmethyl)trimethylammonium iodide 5a, according to Lindsay et al (Lindsay, J. K.; Hauser, C. R. *J. Org. Chem.* 1957, 22, 355-358), $K_2CO_3$ and 18-crown-6 in acetonitrile. N-(1-(ferrocenyloxy)-2-cyanopropan-2-yl)-4-((trifluoromethyl)thio)benzamide 6a was isolated in a low yield by preparative HPLC.

Example 2: Synthesis of 2-cyano-2-(4-((trifluoromethyl)thio)benzamido)propyl ferrocenoate (Compound 8a)

The proposed synthetic pathway is depicted in Scheme 7.

Scheme 7: NEt$_3$, dichloromethane, overnight, r.t., 73%.

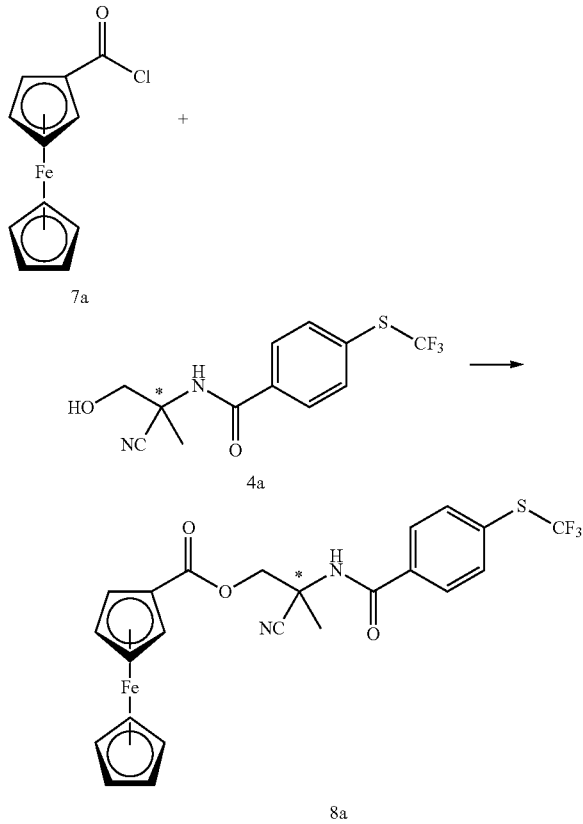

Ferrocene carboxylchloride 7a was treated with triethylamine and N-(2-cyano-1-hydroxypropan-2-yl)-4-((trifluoromethyl)thio)benzamide 4a in dichloromethane to afford 2-cyano-2-(4-((trifluoromethyl)thio)benzamido)propyl ferrocenoate 8a in 73% yield.

Syntheses and Characterization

2-Amino-2-hydroxymethylproprionitrile 3a

2-Amino-2-hydroxymethylproprionitrile 3a was prepared following the procedure published by Gauvry et al (WO2005/044784 A1).

IR (KBr, cm$^{-1}$): 3329s, 3286s, 3205s, 2985s, 2935s, 2858s, 2756w, 2229m, 1625s, 1476m, 1457m, 1383m, 1368w, 1348w, 1269m, 1178s, 1093s, 1065s, 1044s, 963m, 934s, 888m, 785m, 626w, 465m.

$^1$H NMR (400 MHz, MeOD): δ/ppm=3.51 (dd, $^2$J=11.2 Hz, $^2$J=10.8 Hz, 2H, CH$_2$), 1.40 (s, 3H, CH$_3$).

$^{13}$C NMR (400 MHz, CDCl$_3$): δ/ppm=124.4, 69.8, 53.1, 23.9.

ESI-MS: m/z (%)=101.07 ([M+H]+, 100), 83.06 ([M−H$_2$O]$^+$, 64).

HR ESI-MS: calc. for C$_4$H$_9$N$_2$O ([M+H]$^+$) m/z (%)=101.07088. found m/z (%)=101.07094.

N-(2-cyano-1-hydroxypropan-2-yl)-4-((trifluoromethyl)thio)benzamide 4a

After dissolving 2-amino-2-hydroxymethylproprionitrile 1a (0.05 g, 0.50 mmol) in dry dichloromethane (5 mL), NEt$_3$ (70 μl, 0.5 mmol) and 4-(trifluoromethylthio)benzoyl chloride (84 μl, 0.5 mmol) were added and the reaction mixture was stirred for 2 h at room temperature. The solution was extracted with a 1M aqueous solution of hydrochloric acid (2×5 mL). The organic layer was dried over MgSO$_4$, filtered and the solvent was evaporated under reduced pressure. The residue was suspended in a 1M aqueous solution of NaOH (10 mL) and stirred for 1.5 h at room temperature before THF (10 mL) was added. The solution was stirred for an additional hour. The solvent was evaporated under reduced pressure and the residue was extracted with CH$_2$Cl$_2$ (3×10 mL). The combined organic layers were dried over MgSO$_4$, filtered and the solvent was evaporated under reduced pressure to give N-(2-cyano-1-hydroxypropan-2-yl)-4-((trifluoromethyl)thio)benzamide 1b as colourless solid. Yield: 32%.

IR (KBr, cm$^{-1}$): 3418s, 3288w, 3053w, 2935w, 2845w, 1658m, 1616w, 1591w, 1542m, 1482w, 1456w, 1395w, 1317w, 1135m, 1115m, 1081m, 1012w, 925w, 844w, 763w, 623w.

$^1$H NMR (500 MHz, MeOD): δ/ppm=7.98 (d, $^3$J=7 Hz, 2H, arom. H), 7.84 (d, $^3$J=7 Hz, 2H, arom. H), 3.97 (dd, $^2$J=11 Hz, $^2$J=10.5 Hz, 2H, CH$_2$), 1.8 (s, 3H, CH$_3$).

$^{13}$C NMR (500 MHz, MeOD): δ/ppm=167.2, 136.0, 134.9, 129.4, 129.3, 128.5, 119.7, 66.6, 52.8, 21.7. $^{19}$F NMR (500 MHz, CDCl$_3$): δ/ppm=−39.0.

ESI-MS: m/z (%)=327.04 ([M+Na]$^+$, 100), 305.06 ([M+H]$^+$, 21).

HR ESI-MS: calc. for C$_{12}$H$_{12}$F$_3$N$_2$O$_2$S ([M+H]$^+$) m/z (%)=305.05626. found m/z (%)=305.05661.

(Ferrocenylmethyl)trimethylammonium iodide 5a (Ferrocenylmethyl)trimethylammonium iodide 1c was prepared according to Lindsay et al (Lindsay, J. K.; Hauser, C. R. *J. Org. Chem.* 1957, 22, 355-358).

Chlorocarbonyl ferrocene 7a

The synthesis of chlorocarbonyl ferrocene was adapted from a procedure of Witte et al. and Cormode et al. (Witte, P.; Lai, T. K.; Waymouth, R. M. *Organometallics* 1999, 18, 4147-4155 and Cormode, D. P.; Evans, A. J.; Davis, J. J.; Beer, P. D. *Dalton Trans.* 2010, 39, 6532-6541).

Ferrocene (6.0 g, 32 mmol) and potassium tert-butoxide (0.46 g, 4.08 mmol) were completely dissolved in dry THF (300 mL). The orange solution was cooled to −78° C. when tert-butyllithium (34.0 mL, 64.5 mmol, 1.9 M in pentane) was added dropwise over a period of 15 min, with the temperature maintained below −70° C. The reaction mixture was stirred at −78° C. for 1 h and then poured on a slurry of dry ice (excess) and diethyl ether. The mixture was warmed to room temperature overnight and extracted with an aqueous solution of sodium hydroxide (0.75 N, 4×250 mL). The combined aqueous layers were neutralized with hydrochloric acid (pH>4) and the resulting orange solid was extracted with Et$_2$O (4×250 mL) until the organic layer remained colourless. The combined organic layers were filtered to remove traces of ferrocenedicarboxylic acid, dried over MgSO$_4$, filtered and the solvent was evaporated under reduced pressure to give ferrocenecarboxylic acid as an orange solid in 35% yield. After suspending the ferrocenecarboxylic acid (462 mg, 2.01 mmol) in dry CH$_2$Cl$_2$ (23 mL), oxalyl chloride (1100 μL, 13.64 mmol) in dry CH$_2$Cl$_2$ (10 mL) was added dropwise to the reaction mixture whereby the orange suspension turned dark red. The reaction mixture was refluxed for 2 h and then stirred overnight at room temperature. The solvent was then removed under vacuum. The product was not purified and used immediately for the next synthetic step.

Compound 8a-11a were synthesized in a similar fashion. In a round-bottomed flask, 1.5 equivalents of the corresponding activated chlorocarboxylic acid and 1 equivalent of the alcohol were dissolved in dry dichloromethane. To this reaction mixture 1.5 equivalents of triethylamine was added and the reaction was stirred at room temperature overnight. The reaction solution was then evaporated to dryness and the crude product was purified using column chromatography on silica to yield the desired products (8a 11a).

Compound 8a:
$^1$H NMR (500 MHz, Acetone): δ/ppm=8.41 (s, 1H, NH), 8.06 (d, $^3$J=8.5 Hz, 2H, arom. H), 7.86 (d, $^3$J=8 Hz, 2H, arom. H), 4.85-4.84 (m, 2H, $C_5H_4$), 4.69 (dd, $^2$J=11 Hz, $^2$J=10.5 Hz, 2H, $CH_2$), 4.51-4.50 (m, 2H, $C_5H_4$), 4.23 (s, 5H, $C_5H_5$), 1.97 (s, 3H, $CH_3$).
Elemental Analysis: calcd. for $C_{23}H_{19}F_3FeN_2O_3S$: C, 53.50; H, 3.71; N, 5.43. Found C, 53.31; H, 3.68; N, 5.41.

Compound 8b:
$^1$H NMR (500 MHz, $CD_3CN$): δ/ppm=8.10 (d, $^3$J=8.5 Hz, 2H, arom. H), 7.96 (d, $^3$J=8.5 Hz, 2H, arom. H), 7.68 (s, 1H, NH), 4.84-4.83 (m, 2H, $C_5H_4$, 4.58 (dd, $^2$J=11 Hz, 2H, $CH_2$), 4.49-4.48 (m, 2H, $C_5H_4$), 4.19 (s, 5H, $C_5H_5$), 1.88 (s, 3H, $CH_3$).
Elemental Analysis: calcd. for $C_{23}H_{19}F_3FeN_2O_4S$: C, 51.90; H, 3.60; N, 5.26. Found C, 52.06; H, 3.86; N, 4.99.

Compound 8c:
$^1$H NMR (500 MHz, Acetone): δ/ppm=8.69 (s, 1H, NH), 8.34 (d, $^3$J=8.5 Hz, 2H, arom. H), 8.28 (d, $^3$J=8.5 Hz, 2H, arom. H), 4.85-4.84 (m, 2H, $C_5H_4$), 4.70 (dd, $^2$J=10.5 Hz, $^2$J=11 Hz, 2H, $CH_2$), 4.51-4.50 (m, 2H, $C_5H_4$), 4.24 (s, 5H, $C_5H_5$), 1.98 (s, 3H, $CH_3$).
Elemental Analysis: calcd. for $C_{23}H_{19}F_3FeN_2O_5S$: C, 50.38; H, 3.49; N, 5.11. Found C, 50.71; H, 3.57; N, 5.05.

Compound 8d:
$^1$H NMR (500 MHz, $CD_3CN$): δ/ppm=7.95 (d, $^3$J=8.5 Hz, 2H, arom. H), 7.54 (s, 1H, NH), 7.41 (d, $^3$J=8 Hz, 2H, arom. H), 4.83-4.82 (m, 2H, $C_5H_4$), 4.56 (dd, $^2$J=11 Hz, $^2$J=11 Hz, 2H, $CH_2$), 4.49-4.48 (m, 2H, $C_5H_4$), 4.19 (s, 5H, $C_5H_5$), 1.86 (s, 3H, $CH_3$).
Elemental Analysis: calcd. for $C_{23}H_{19}F_3FeN_2O_4$: C, 55.22; H, 3.83; N, 5.60. Found C, 55.36; H, 3.81; N, 5.53.

Compound 8e:
$^1$H NMR (500 MHz, Acetone): δ/ppm=8.48 (s, 1H, NH), 8.15 (d, $^3$J=8.5 Hz, 2H, arom. H), 7.86 (d, $^3$J=8.5 Hz, 2H, arom. H), 4.85-4.84 (m, 2H, $C_5H_4$), 4.69 (dd, $^2$J=11 Hz, $^2$J=11 Hz, 2H, $CH_2$), 4.51-4.50 (m, 2H, $C_5H_4$), 4.24 (s, 5H, $C_5H_5$), 1.97 (s, 3H, $CH_3$).
Elemental Analysis: calcd. for $C_{23}H_{19}F_3FeN_2O_3$: C, 57.05; H, 3.95; N, 5.78. Found C, 57.61; H, 3.87; N, 5.94.

Compound 8f:
$^1$H NMR (500 MHz, Acetone): δ/ppm=8.09 (s, 1H, NH), 7.88 (d, $^3$J=8.5 Hz, 2H, arom. H), 7.36 (d, $^3$J=8.5 Hz, 2H, arom. H), 4.85-4.84 (m, 2H, $C_5H_4$), 4.67 (dd, $^2$J=11 Hz, $^2$J=11 Hz, 2H, $CH_2$), 4.51-4.49 (m, 2H, $C_5H_4$), 4.23 (s, 5H, $C_5H_5$), 2.54 (s, 3H, $CH_3$), 1.94 (s, 3H, $CH_3$).
Elemental Analysis: calcd. for $C_{23}H_{22}FeN_2O_3S$: C, 59.75; H, 4.80; N, 6.06. Found C, 59.60; H, 4.73; N, 5.99.

Compound 8g:
$^1$H NMR (400 MHz, Acetone): δ/ppm=8.18 (s, 1H, NH), 8.04-8.00 (m, 2H, arom. H), 7.29-7.24 (m, 2H, arom. H), 4.85-4.83 (m, 2H, $C_5H_4$), 4.68 (dd, $^2$J=11 Hz, $^2$J=11 Hz, 2H, $CH_2$), 4.51-4.50 (m, 2H, $C_5H_4$), 4.23 (s, 5H, $C_5H_5$), 1.95 (s, 3H, $CH_3$).
Elemental Analysis: calcd. for $C_{22}H_{19}FeFN_2O_3$: C, 60.85; H, 4.41; N, 6.45. Found C, 61.16; H, 4.37; N, 6.39.

Compound 8h:
$^1$H NMR (400 MHz, Acetone): δ/ppm=8.24 (s, 1H, NH), 7.96 (d, $^3$J=10.8 Hz, 2H, arom. H), 7.54 (d, $^3$J=13.2 Hz, 2H, arom. H), 4.85-4.84 (m, 2H, $C_5H_4$), 4.68 (dd, $^2$J=10.8 Hz, $^2$J=10.8 Hz, 2H, $CH_2$), 4.51-4.50 (m, 2H, $C_5H_4$), 4.23 (s, 5H, $C_5H_5$), 1.95 (s, 3H, $CH_3$).
Elemental Analysis: calcd. for $C_{22}H_{19}FeClN_2O_3$: C, 58.63; H, 4.25; N, 6.22. Found C, 58.33; H, 4.11; N, 6.09.

Compound 8i:
$^1$H NMR (400 MHz, Acetone): δ/ppm=8.24 (s, 1H, NH), 7.90-7.88 (m, 2H, arom. H), 7.72-7.69 (m, 2H, arom. H), 4.86-4.83 (m, 2H, $C_5H_4$), 4.67 (dd, $^2$J=10.8 Hz, $^2$J=10.8 Hz, 2H, $CH_2$), 4.52-4.50 (m, 2H, $C_5H_4$), 4.23 (s, 5H, $C_5H_5$), 1.95 (s, 3H, $CH_3$).
Elemental Analysis: calcd. for $C_{22}H_{19}FeBrN_2O_3$: C, 53.37; H, 3.87; N, 5.66. Found C, 53.42; H, 3.84; N, 5.61.

Compound 8j:
$^1$H NMR (500 MHz, Acetone): δ/ppm=8.25 (s, 1H, NH), 7.91 (d, $^3$J=8.5 Hz, 2H, arom. H), 7.73 (d, $^3$J=8.5 Hz, 2H, arom. H), 4.85-4.84 (m, 2H, $C_5H_4$), 4.67 (dd, $^2$J=11 Hz, $^2$J=10.5 Hz, 2H, $CH_2$), 4.51-4.50 (m, 2H, $C_5H_4$), 4.23 (s, 5H, $C_5H_5$), 1.95 (s, 3H, $CH_3$).
Elemental Analysis: calcd. for $C_{22}H_{19}FeIN_2O_3$: C, 48.74; H, 3.53; N, 5.17. Found C, 48.64; H, 3.49; N, 4.99.

Compound 8k:
$^1$H NMR (400 MHz, $CDCl_3$): δ/ppm=7.86-7.76 (m, 5H, arom. H and NH), 5.24-5.22 (m, 2H, $C_5H_4$), 4.80-4.78 (m, 2H, $C_5H_4$), 4.72 (d, $^2$J=12 Hz, 1H, $CH_2$), 4.48 (s, 5H, $C_5H_5$), 4.35 (d, $^2$J=12 Hz, 1H, $CH_2$), 1.87 (s, 3H, $CH_3$).
Elemental Analysis: calcd. for $C_{23}H_{19}F_3RuN_2O_3S$: C, 49.19; H, 3.41; N, 4.99. Found C, 49.35; H, 3.39; N, 4.94.

Compound 10a:
$^1$H NMR (500 MHz, Acetone): δ/ppm=7.99 (d, $^3$J=8.5 Hz, 2H, arom. H), 7.90 (d, $^3$J=8.0 Hz, 2H, arom. H), 7.55 (s, 1H, NH), 6.63 (s, 1H, CH), 4.74 (dd, $^2$J=11 Hz, $^2$J=11.5 Hz, 2H, $CH_2$), 1.91 (s, 3H, $CH_3$).
Elemental Analysis: calcd. for $C_{21}H_{11}Co_2F_3N_2O_9S$: C, 39.27; H, 1.73; N, 4.36. Found C, 39.63; H, 2.23; N, 4.44.

Compound 11a:
$^1$H NMR (500 MHz, $CDCl_3$): δ/ppm=7.82 (d, $^3$J=8.5 Hz, 2H, arom. H), 7.74 (d, $^3$J=8.5 Hz, 2H, arom. H), 6.99 (s, 1H, NH), 5.57-5.54 (m, 2H, $C_5H_4$), 4.89-4.88 (m, 2H, $C_5H_4$), 4.66 (dd, $^2$J=12 Hz, $^2$J=11.5 Hz, 2H, $CH_2$), 1.89 (s, 3H, $CH_3$).
Elemental Analysis: calcd. for $C_2H_{17}MnF_3N_2O_6S$: C, 46.94; H, 3.19; N, 5.21. Found C, 47.39; H, 2.90; N, 5.11.

Cytotoxicity and Nematocidal Studies:
The toxicity towards human cervical cancer HeLa was investigated using the fluorometric cell viability assay (Resazurin) (Ahmed, S. A.; Gogal, R. M. J.; Walsh, J. E. *J. Immunol. Methods* 1994, 170, 211-224). For compounds which were found to be toxic towards HeLa cells, their cytotoxicity towards the human lung fibroblasts MRC-5 was also tested (see table 1).

*C. elegans* is widely used as a tool in the pharmaceutical and biotechnology industry to test the efficacy of compounds against nematodes and other organisms (cf. Divergence, Inc.—now acquired from the Montsanto Company), which has the major advantage that the modes/mechanisms of action and associated phenotypes can be fully characterised as well as resistance development assessed, Given that *C. elegans* and socioeconomic strongylid nematodes belong to Glade V of the phylum Nematoda (Blaxter et al., 1998—*Nature*), there is a high likelihood that drug action will be effective/effected in strongylid nematodes.

TABLE 1 shows the toxicity towards human cervical cancer HeLa and towards the human lung fibroblasts MRC-5 using the fluorometric cell viability assay.

| Compound | $IC_{50}$ in HeLa/ μmol/l | $IC_{50}$ in MRC-5/ μmol/l |
|---|---|---|
| 8a | 32.89 | 23.87 |

The activity against *Haemontus Contortus, Dirofilaria immitis* and *Trychostrongylus colubriformis* was tested and the results are shown in table 2.

As can be seen in Table 2, interesting EC values could be obtained, especially on *Haemontus contortus*.

The invention claimed is:
1. A compound characterized by a general formula (1),

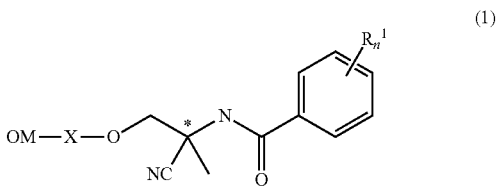

(1)

wherein X is a group described by a general formula —$K_p$—$F_l$—$K_q$—, wherein
$F_l$ is —C(=O)—, —C(=S)—, with l being 0 or 1,
$K_p$ is a $C_p$-alkyl with p being 0, 1, 2, 3 or 4,
$K_q$ is a $C_q$-alkyl with q being 0, 1, 2, 3 or 4, and wherein

TABLE 2 shows the activity against *Haemontus Contortus, Dirofilaria immitis* and *Trychostrongylus colubriformis*.

| Compound | Activity against *Haemontus Contortus* | Activity against *Dirofilaria immitis* | Activity against *Trychostrongylus colubriformis* |
|---|---|---|---|
|  | $EC_{90}$ at up to 10 μg/mL | $EC_{85}$ at up to 10 μg/mL | $EC_{65}$ at up to 10 μg/mL |
|  | $EC_{40}$ at up to 10 μg/mL | $EC_{45}$ at up to 10 μg/mL | $EC_{30}$ at up to 10 μg/mL |
|  | $EC_{60}$ at up to 10 μg/mL | — | $EC_{50}$ at up to 10 μg/mL |
|  | $EC_{60}$ at up to 10 μg/mL | — | $EC_{50}$ at up to 10 μg/mL | n of $R^1_n$ is 0, 1, 2, 3, 4 or 5, and
each $R^1$ independently from any other $R^1$ is —C(=O)OR$^2$, —C(=O)NR$^2_2$, —C(=O)SR$^2$, —C(=S)OR$^2$, —C(NH)NR$^2_2$, —CN$_4$H$_2$, —NR$^2_2$, —C(=O)R$^2$, —C(=S)R$^2$, —OR$^2$, —SR$^2$, —CF$_3$, —OCF$_3$, —SCF$_3$, —SOCF$_3$, —SO$_2$CF$_3$, —CN, —NO$_2$, —F, —Cl, —Br or —I, with each $R^2$ independently from any other $R^2$ being a hydrogen or C$_1$-C$_4$ alkyl, and wherein OM is an organometallic compound independently selected from the group of an unsubstituted or substituted metal sandwich compound, an unsubstituted or substituted half metal sandwich compound or a metal carbonyl compound.

2. The compound according to claim 1, wherein n of $R^1_n$ is 1 or 2 and each $R^1$ independently from any other $R^1$ is —CN, —CF$_3$, —OCF$_3$, —SCF$_3$, —SOCF$_3$, —SO$_2$CF$_3$, —F, —Cl, —Br or —I, and wherein in particular each $R^1$ independently from any other $R^1$ is —CN, —CF$_3$, —SCF$_3$, —SOCF$_3$ or —SO$_2$CF$_3$.

3. The compound according to claim 1, wherein n of $R^1_n$ is 1 or 2 and each $R^1$ independently from any other $R^1$ is —F, —Cl, —Br or —I.

4. The compound according to claim 1, wherein n of $R^1_n$ is 2 and each $R^1$ independently from any other $R^1$ is —CN, —CF$_3$, —OCF$_3$, —F, —Cl, —Br or —I and wherein in particular each $R^1$ independently from any other $R^1$ is —CN or —CF$_3$.

5. The compound according to claim 1, wherein n of $R^1_n$ is 1 and $R^1$ is —CN, —CF$_3$, —OCF$_3$, —SCF$_3$, —SOCF$_3$, —SO$_2$CF$_3$, —F, —Cl, —Br or —I, and wherein in particular $R^1$ is —SCF$_3$, —SOCF$_3$ or —SO$_2$CF$_3$.

6. The compound according to claim 1, wherein n is 2 and one of the two $R^1$ is in ortho and the other $R^1$ is in meta position to the attachment position of the benzene moiety, and wherein in particular one of the two $R^1$ is —CF$_3$ in ortho and the other $R^1$ is —CN in meta position to the attachment position of the benzene moiety.

7. The compound according to claim 1, wherein n is 1 and $R^1$ is in para position to the attachment position of the benzene moiety, and wherein in particular $R^1$ is —SCF$_3$, —SOCF$_3$ or SO$_2$CF$_3$ in para position to the attachment position of the benzene moiety.

8. The compound according to claim 1, wherein
l of $F_l$ is 0, q of $K_q$ and p of $K_p$ is 0 or
l of $F_l$ is 0, q of $K_q$ is 0 and $K_p$ is C$_1$-alkyl or
$F_l$ is —C(=O)— with l being 1, q of $K_q$ and p of K, are 0 or
$F_l$ is —C(=O)— with l being 1, q of $K_q$ is 0 and $K_p$ is C$_1$-alkyl.

9. The compound according to claim 1, wherein OM is an organometallic compound according to the general formula (2a),

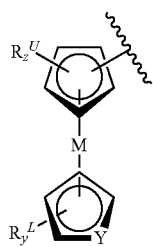

(2a)

wherein M is a metal selected from Fe, Ru, Co, Ni, Cr, Os or Mn, and
Y is C or N, and
z of $R_z^U$ is 0, 1, 2, 3 or 4, and y of $R_y^L$ is 0, 1, 2, 3, 4 or 5 and
each $R^L$ and each $R^U$ are independently from any other $R^L$ and $R^U$ selected from
an unsubstituted or substituted C$_1$-C$_{10}$ alkyl, an unsubstituted or substituted C$_1$-C$_{10}$ alkenyl, an unsubstituted or substituted C$_1$-C$_{10}$ alkynyl, an unsubstituted or substituted C$_3$-C$_8$ cycloalkyl, an unsubstituted or substituted C$_1$-C$_{10}$ alkoxy, an unsubstituted or substituted C$_3$-C$_8$ cycloalkoxy,
an unsubstituted or substituted C$_6$-C$_{14}$ aryl,
an unsubstituted or substituted 5- to 10-membered heteroaryl, wherein 1 to 4 ring atoms are independently selected from nitrogen, oxygen or sulfur,
an unsubstituted or substituted 5- to 10-membered heteroalicyclic ring, wherein 1 to 3 ring atoms are independently nitrogen, oxygen or sulfur,
—OR$^3$, —SR$^3$, —C(O)R$^3$, —C(S)R$^3$, —C(O)OR$^3$, —C(S)OR$^3$, —C(O)SR$^3$, —C(O)NR$^3$R$^4$, —NR$^3$R$^4$, —S(O)$_2$R$^3$, —S(O)$_2$OR$^3$ and —S(O)$_2$NR$^3$R$^4$,
wherein
$R^3$ and $R^4$ are independently selected from the group consisting of hydrogen, unsubstituted C$_1$-C$_4$ alkyl, and C$_1$-C$_4$ alkyl substituted with C$_1$-C$_4$ alkoxy.

10. The compound according to claim 9, wherein each $R^L$ and each $R^U$ are independently from any other $R^L$ and $R^U$ selected from
—OR$^3$, —SR$^3$, —C(O)R$^3$, —C(S)R$^3$, —C(O)OR$^3$, —C(S)OR$^3$, —C(O)SR$^3$—C(O)NR$^3$R$^4$, —NR$^3$R$^4$, —S(O)$_2$R$^3$, —S(O)$_2$OR$^3$, and —S(O)$_2$NR$^3$R$^4$,
wherein
$R^3$ and $R^4$ are independently selected from the group consisting of hydrogen, unsubstituted C$_1$-C$_4$ alkyl, and C$_1$-C$_4$ alkyl substituted with C$_1$-C$_4$ alkoxy.

11. The compound according to claim 9, wherein M is selected from the group of Fe, Ru or Co, wherein in particular M is Fe; and/or
wherein Y is C; and/or
wherein y and z are 0.

12. The compound according claim 1, wherein OM is an organometallic compound according to the general formula (2b),

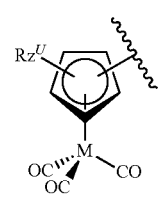

(2b)

wherein M is a metal selected from the group of Mn, Re or Tc, and
z of $R_z^U$ is 0, 1, 2, 3 or 4, and
each $R^U$ is independently from any other $R^U$ selected from
an unsubstituted or substituted C$_1$-C$_{10}$ alkyl, an unsubstituted or substituted C$_1$-C$_{10}$ alkenyl, an unsubstituted or substituted C$_1$-C$_{10}$ alkynyl, an unsubstituted or substituted C$_3$-C$_8$ cycloalkyl, an unsubstituted or substituted C$_1$-C$_{10}$ alkoxy, an unsubstituted or substituted C$_3$-C$_8$ cycloalkoxy,
an unsubstituted or substituted C$_6$-C$_{14}$ aryl, an unsubstituted or substituted 5- to 10-membered heteroaryl, wherein 1 to 4 ring atoms per QS are independently selected from nitrogen, oxygen or sulfur, an unsubstituted or substituted 5- to 10-membered heteroalicyclic ring, wherein 1 to 3 ring atoms are independently nitrogen, oxygen or sulfur, —$OR^3$, —$SR^3$, —$C(O)R^3$, —$C(S)R^3$, —$C(O)OR^3$, —$C(S)OR^3$, —$C(O)SR^3$, —$C(O)NR^3R^4$, —$NR^3R^4$, —$S(O)_2R^3$, —$S(O)_2OR^3$, and —$S(O)_2NR^3R^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

13. The compound according claim 1, wherein OM is an organometallic compound according to the general formula (2c),

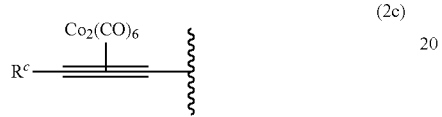

(2c)

wherein $R^c$ is selected from hydrogen, an unsubstituted or substituted $C_1$-$C_{10}$ alkyl an unsubstituted or substituted $C_1$-$C_{10}$ alkenyl, an unsubstituted or substituted $C_1$-$C_{10}$ alkynyl, an unsubstituted or substituted $C_3$-$C_8$ cycloalkyl, an unsubstituted or substituted $C_1$-$C_{10}$ alkoxy, an unsubstituted or substituted $C_3$-$C_8$ cycloalkoxy, an unsubstituted or substituted $C_6$-$C_{14}$ aryl, an unsubstituted or substituted 5- to 10-membered heteroaryl, wherein 1 to 4 ring atoms are independently selected from nitrogen, oxygen or sulfur, an unsubstituted or substituted 5- to 10-membered heteroalicyclic ring, wherein 1 to 3 ring atoms are independently nitrogen, oxygen or sulfur, —$OR^3$, —$SR^3$, —$C(O)R^3$, —$C(S)R^3$, —$C(O)OR^3$, —$C(S)OR^3$, —$C(O)SR^3$, —$C(O)NR^3R^4$, —$NR^3R^4$, —$S(O)_2R^3$, —$S(O)_2OR^3$, and —$S(O)_2NR^3R^4$, wherein $R^3$ and $R^4$ are independently selected from the group consisting of hydrogen, unsubstituted $C_1$-$C_4$ alkyl, and $C_1$-$C_4$ alkyl substituted with $C_1$-$C_4$ alkoxy.

14. A compound according to claim 1 for use in a method of treatment of disease.

15. A compound according to claim 1 for use in a method for treatment of infections by helminths, or for use in a method to suppress plant helminths.

* * * * *